(12) United States Patent
Higuchi

(10) Patent No.: US 8,822,232 B2
(45) Date of Patent: Sep. 2, 2014

(54) DIAGNOSIS, PREVENTION AND TREATMENT OF DISORDERS CHARACTERIZED BY UNDESIRABLE CELL PROLIFERATION

(76) Inventor: Maria de Lourdes Higuchi, Sao-Paulo (BR)

(*) Notice: Subject to any disclaimer, the term of this patent is extended or adjusted under 35 U.S.C. 154(b) by 93 days.

(21) Appl. No.: 13/073,838

(22) Filed: Mar. 28, 2011

(65) Prior Publication Data
US 2011/0262961 A1 Oct. 27, 2011

Related U.S. Application Data

(60) Continuation-in-part of application No. 12/770,487, filed on Apr. 29, 2010, now Pat. No. 7,914,781, which is a division of application No. 12/033,193, filed on Feb. 19, 2008, now Pat. No. 7,732,410, which is a continuation-in-part of application No. 10/952,003, filed on Sep. 28, 2004, now Pat. No. 7,335,638, which is a continuation-in-part of application No. PCT/BR03/00049, filed on Mar. 28, 2003.

(60) Provisional application No. 60/890,977, filed on Feb. 21, 2007.

(51) Int. Cl.
G01N 33/536 (2006.01)
G01N 33/543 (2006.01)

(52) U.S. Cl.
USPC .......................................... 436/536; 436/543

(58) Field of Classification Search
USPC .................................................. 436/536, 543
See application file for complete search history.

(56) References Cited

U.S. PATENT DOCUMENTS

| | | | |
|---|---|---|---|
| 5,596,091 A | 1/1997 | Switzer | |
| 6,281,199 B1 | 8/2001 | Gupta | |
| 7,108,851 B2 | 9/2006 | Higuchi et al. | |
| 7,335,638 B2 | 2/2008 | Higuchi | |
| 7,674,832 B2 | 3/2010 | Higuchi | |
| 7,732,410 B2 | 6/2010 | Higuchi | |
| 7,906,114 B2 | 3/2011 | Higuchi | |
| 7,914,781 B2 | 3/2011 | Higuchi | |
| 2003/0124109 A1 | 7/2003 | Higuchi et al. | |
| 2005/0142116 A1 | 6/2005 | Higuchi | |
| 2009/0068167 A1 | 3/2009 | Higuchi | |
| 2012/0114627 A1 | 5/2012 | Higuchi | |

FOREIGN PATENT DOCUMENTS

| WO | WO/02/02050 | 1/2002 |
|---|---|---|
| WO | WO/03/082324 | 10/2003 |
| WO | WO/2006/034560 | 4/2006 |

OTHER PUBLICATIONS

U.S. Appl. No. 10/086,913, Mar. 21, 2006 Notice of Allowance.
U.S. Appl. No. 10/086,913, Nov. 9, 2005 Request for Continued Examination (RCE).
U.S. Appl. No. 10/086,913, Oct. 24, 2005 Notice of Allowance.
U.S. Appl. No. 10/086,913, Jul. 29, 2005 Response to Non-Final Office Action.
U.S. Appl. No. 10/086,913, Jan. 27, 2005 Non-Final Office Action.
U.S. Appl. No. 10/952,003, Oct. 1, 2007 Notice of Allowance.
U.S. Appl. No. 10/952,003, Sep. 7, 2007 Request for Continued Examination (RCE).
U.S. Appl. No. 10/952,003, Jul. 30, 2007 Notice of Allowance.
U.S. Appl. No. 10/952,003, Apr. 23, 2007 Response to Non-Final Office Action.
U.S. Appl. No. 10/952,003, Jan. 23, 2007 Non-Final Office Action.
U.S. Appl. No. 12/033,204, Oct. 20, 2009 Notice of Allowance.
U.S. Appl. No. 12/717,013, Oct. 18, 2010 Notice of Allowance.
U.S. Appl. No. 12/717,013, Sep. 24, 2010 Supplemental Amendment.
U.S. Appl. No. 12/717,013, Sep. 20, 2010 Request for Continued Examination (RCE).
U.S. Appl. No. 12/717,013, Jun. 21, 2010 Notice of Allowance.
U.S. Appl. No. 12/033,193, Jan. 8, 2010 Notice of Allowance.
U.S. Appl. No. 12/770,487, Nov. 2, 2010 Notice of Allowance.
U.S. Appl. No. 12/770,487, Oct. 18, 2010 Supplemental Amendment.
U.S. Appl. No. 12/770,487, Oct. 11, 2010 Response to Non-Final Office Action.
U.S. Appl. No. 12/770,487, Sep. 20, 2010 Non-Final Office Action.
Agusti, et al., 1997, "The trans-sialidase of *Trypanosome cruzi* is anchored by two different lipids," Glycobiology, vol. 7, No. 6: p. 731-735.
Aiello, et al., 2002, "A possible role for complement in the pathogenesis of chronic chagasic cardiomyopathy," Journal of Pathology, vol. 197: p. 224-229.
Akira et al., "Toll-like receptors: critical proteins linking innate and acquired immunity," Nature Immunol. 2:675-680(2001).
Amaya, et al., 2004, "Structural Insights into the catalytic mechanism of *Trypanosoma cruzi* trans-sialidase," Structure, vol. 12: p. 775-784.
Amend et al., "Energetics of overall metabolic reactions of thermophilic and hyperthermophilic archaea and bacteria," F.E.M.S, Microbiol. Rev. 25: 175-243 (2001).
Baseman, et al., 1982, "Sialic acid residues mediate *Mycoplasma pneumoniae* attachment to human and sheep erythrocytes," Infect. Immun., vol. 38, No. 1: p. 389-391.
Berbec, et al., 1999, "Total serum sialic acid concentration as a supporting marker of malignancy in ovarian neoplasia," Eur. J. Gynaecol on Col., vol. 20, No. 5-6: p. 389-392.
Blanchard, et al., 1994, "AIDS-associated mycoplasmas," Annu. Rev. Microbiol., vol. 48: p. 687-712.
Bredt, et al., 1982, "Adherence of mycoplasmas: phenomena and possible role in the pathogenesis of disease," Infection, vol. 10, No. 3: p. 199-201.
Briones, et al., 1993, "*Trypanosoma cruzi* trans-sialidase homologue," Accession No. AAC98544, GI:624626, 736 aa.
Buscaglia, et al., 1998, "The repetitive domain of *Trypanosome cruzi* trans-sialidase enhances the immune response against the catalytic domain," J. Infect. Dis., vol. 177, No. 2: p. 431-436.

(Continued)

Primary Examiner — Maryam Monshipouri
(74) Attorney, Agent, or Firm — Baker Botts, L.L.P.

(57) ABSTRACT

The present invention relates to compositions and methods for the reduction of atherosclerotic plaques and the decrease in the level of total serum cholesterol, triglycerides, serum LDL cholesterol, and serum HDL cholesterol. The present invention also relates to methods for the diagnosis, prevention and treatment of atherosclerosis and mycoplasma associated diseases.

4 Claims, 11 Drawing Sheets

(56) References Cited

OTHER PUBLICATIONS

Buscaglia, et al., 1999, "Tandem amino acid repeats from *Trypanosoma cruzi* shed antigens increase the half-life of proteins in blood," Blood, vol. 93: p. 2025-2032.

Buschiazzo, et al., 1996, "Medium scale production and purification to homogeneity of a recombinant trans-sialidase from *Trypanosoma cruzi*," Cell Mol. Biol., vol. 42: p. 703-710.

Buschiazzo, et al., 2002, "The Crystal Structure and Mode of Action of Trans-sialidase, a key enzyme in *Trypanosoma cruzi* pathogenesis," Molecular Cell, vol. 10: p. 757-758.

Campetella, et al., 1994, "A recombinant *Trypanosoma cruzi* trans-sialidase lacking the amino acid repeats retains the enzymatic activity," Mol. Biochem. Parasitol., vol. 64: p. 337-340.

Chandler, et al., 1982, "*Mycoplasma pneumoniae* attachment: competitive inhibition by mycoplasmal binding component and by sialic acid-containing glycoconjugates," Infect. Immun., vol. 38, No. 2: p. 598-603.

Chen et al., "Apoptosis of hepatoma cells SMMC-7721 induced by *Ginkgo biloba* seed polysaccharide," World J. Gastroenterol. 8: 832-6 (2002).

Chen et al., 1986, "Carditis associated with *Mycoplasma pneumoniae* infection," Am. J. Dis. Child., vol. 140: p. 471-472.

Clyde et al., "Tropism for *Mycoplasma gallisepticum* for arterial walls," Proc. Natl. Acad. Sci. U.S.A. 70: 1545-1549 (1973).

Cole, 1997 "*Mycoplasma* interactions with the immune system: implications for disease pathology," http://www.compkarori.com/arthritis/pil6002.htm.

Cole, 1999, "*Mycoplasma*-induced arthritis in animals: relevance to understanding the etiologies of the human rheumatic diseases," Rev. Rhum. Engl. Ed. 66, 1Suppl: p. 45S-49S.

Collier and Clyde, "Relationships between *M. pneumoniae* and human respiratory epithelium," Infect. Immun. 3:694-701 (1971).

Cremona, et al., 1995, "A single tyrosine differentiates active and inactive *Trypanosome cruzi* trans-sialidase," Gene, vol. 160: p. 123-128.

Cremona, et al., 1996, "Effect of primary structure modifications in *Trypanosoma cruzi* neuramindase trans-sialidase activities," Cell. Mol. Biol., vol. 42: p. 697-702.

Dallo, et al., 2000, "Intracellular DNA replication and long term survival of pathogenic *Mycoplasmas*" Microbial Pathogenesis vol. 29: p. 301-309.

Damy et al,. "Coinfection of laboratory rats with *Mycoplasma pulmonis* and *Chlamydia pneumoniae*," Contemp. Top.Am.Assoc. Lab.An.Sci. 42: 52-56 (2003).

Danesch, et al., 1997, "Chronic infections and coronary artery disease: is there a link?" Lancet, vol. 350: p. 430-436.

Fagundes RQ. Study of co-participation of natural infection by *Chlamydophila pneumoniae* and *Mycoplasma pneumoniae* in experimental atherogenesis in rabbits. Doctoral thesis presented at the Heart Institute of Clinical Hospital, in the Cardiology Sciences Post Graduation Program of São Paulo University School of Medicine, Mar. 17, 2006. (The Summary is in the English language).

Farraji, et al., 1997, "*Mycoplasma*-associated pericarditis," Mayo Clin. Proc., vol. 72: p. 33-36.

Fearon et al., "Cancer cachexia," Int. J. Cardiol 85: 73-81 (2002).

Feng Shaw-Huey, et al., 1999, "*Mycoplasma* infections prevent apoptosis and induce malignant transformation of interleukin-3-dependent 32D hematopoietic cells," Mol. Cel. Biol., vol. 19, No. 12: p. 7995-8002.

Florin THJ et al., "Shared and unique environmental factors determine the ecology of methanogens in humans and rats," Am. J. Gastroenterol, 95: 2872-2879 (2000).

Fu et al., 1998, "Middle cerebral artery occlusion after recent *Mycoplasma pneumoniae* infection," J. Neurol. Sci., vol. 157: p. 113-115.

Gabridge and Taylor-Robinson, "Interaction of *Mycoplasma pneumoniae* with human lung fibroblasts: role of receptor sites," Infect. Immun. 25:455-459 (1979).

Giles et al., "Androgenetic alopecia and prostate cancer: findings from an Australian case-control study," Cancer Epidemiol. Biomarkers Prev 11: 549-553 (2002).

Glasgow and Hill, "Interactions of *Mycoplasma gallisepticum* with sialyl glycoproteins," Infect. Immun. 30:353-361 (1980).

Gurfinkel, et al., 1997, "IgG antibodies to chlamydial and *Mycoplasma* infection plus C-reactive protein related to poor outcome in unstable angina," Arch. Inst. Cardiol. Mex., vol. 67: p. 462-468.

Hansen, et al., 1981, "Characterization of hemadsorption-negative mutants of *Mycoplasma pneumoniae*," Infect. Immun., vol. 32: p. 127-136.

Higuchi et al., "*Mycoplasma pneumoniae* and *Chlamydia pneumoniae* in calcified nodules of aortic stenotic valves," Rev Inst Med trop S.Paulo 44:209-212 (2002).

Higuchi et al., 2000, "Detection of *Mycoplasma pneumoniae* and *Chlamydia pneumoniae* in ruptured atherosclerotic plaques," Braz. J. Med. Biol. Res. 33:1023-1026.

Higuchi et al., 2006, "Co-infection ratios versus inflammation, growth factors and progression of early atheromas," APMIS, 114(5):338-44.

Higuchi, et al., 1987, "The role of active myocarditis in the development of heart failure in chronic chagas disease: a study based on endomycardial biopsies," Clin. Cardiol., vol. 10: p. 665-670.

Higuchi, et al., 1997, "Association of an increase in CD8+T cells with the presence of *Trypanosoma cruzi* antigens in chronic human chagasic mycoarditis," Am. J. Trop. Med. Hyg., vol. 56, No. 5: p. 485-489.

Higuchi, et al., 2000, "Great amount of *C. pneumoniae* in ruptured plaque vessel segments at autopsy. A comparative study of stable plaques," Ara. Bras. Cardiol., vol. 74: p. 149-151.

Higuchi, et al., 2003, "Pathophysiology of the heart in chagas' disease: current status and new developments" European Society of Cardiology, pp. 96-107.

Higuchi, et al., 2003, "Coinfection with *Mycoplasma pneumoniae* and *Chlamydia pneumoniae* in ruptured plaques associated with acute myocardia infarction," Arq. Bras, Cardiol., vol. 81, No. 1: p. 12-22.

Higuchi, et al., 2004, "*Trypanosoma cruzi* trans-sialidase as a new therapeutic tool in the treatment of chronic inflammatory disease: possible action against *Mycoplasma* and *Chlamydia*," Medical Hypotheses, vol. 63: p. 616-623.

Horne, et al., 2000, "IgA sero-positivity to *Mycoplasma pneumoniae* predicts the diagnosis of coronary artery disease," J. Am. Coll. Cardiol., vol. 35: p. 321 (abstract).

Howland et al., The surprising archaea. Discovering another domain of life. Oxford University Press. (New York, 2000). (Table of Contents Only).

Huber J et al., "A new phylum of Archaea represented by a nanosized hyperthermophilic symbiont," Nature 417: 63-67 (2002).

Izumikawa et al., 1986, "*Mycoplasma pneumoniae* Attachment to Glutaraldehyde-Treated Human WiDr Cell Cultures," Proc. of the Soc. for Exp. Biol. and Med, vol. 181, No. 4, pp. 507-511.

Kahane et al., 1981, "Attachement of *Mycoplasmas* to epithelium of the host respiratory tract," Isr. J. Med. Sci., vol. 17: p. 589-592.

Kahane, 1983, "Purification of attachment moiety: a review," Yale J. Biol. Med., vol. 53: p. 665-669.

Kaji, et al., 2005, "A Side effect of neuraminidase inhibitor in a patient with liver cirrhosis," J. Infect. Chemother, vol. 11: p. 41-43.

Kloetzel, et al., 1984, "*Trypanosoma cruzi* interaction with macrophages: differences between tissue culture and bloodstream forms." Rev. Inst. Med. Trop. Sao Paulo., vol. 26: p. 179-185.

Krause et al., 1982, "Identification of *Mycoplasma pneumoniae* proteins associated with hemadsorption and virulence," Infect. Immun., vol. 35: p. 809-817.

Laroy, et al., 2000, "Cloning of *Trypanosoma cruzi* trans-Sialidase and Expression in *Pichia pastoris*," Protein Expr. Purif., vol. 20: p. 389-393.

Libby, et al., 1986, "A Neuraminidase from *Tryanosoma cruzi* removes sialic acid from the surface of mammalian myocardial and endothelial cells," J. Clin. Invest., vol. 77: p. 127-135.

(56) References Cited

OTHER PUBLICATIONS

Maida, et al., 1983, "Immunological reactions against *Mycoplasma pneumoniae* in multiple sclerosis: preliminary findings," J. Neurol., vol. 229, No. 2: p. 103-111.

Maniloff et al. Eds., *Mycoplasmas*, Molecular Biology and Pathogenesis. American Society for Microbiology. (Washington, 1992). (Table of Contents).

Maraha, et al., 2000, "Is *Mycoplasma pneumoniae* associated with vascular disease," J. Clin. Microbiol., vol. 38: p. 935-936.

Milner, "A historical perspective on garlic and cancer," J. Nutr. 131: 1027S-1031S. (2001).

Monto, et al., 1999, "Efficacy and Safety of the Neuraminidase Inhibitor Zanamivir in the treatment of Influenza A and B Virus Infections," Journal of Infectious Diseases, vol. 180: p. 254-261.

Muhlradt, "Immunomodulation by *Mycoplasmas*: artifacts, facts and active molecules," in Molecular Biology and Pathogenicity of *Mycoplasmas*. Eds Razin S & Herrman R, 2002, academic Kluwer/Plenum Publishers, New York, p. 445-472.

Neyrolles et al., 1998, "Identification of two glycosylated components of *Mycoplasma penetrans*: a surface-exposed capsular polysaccharide and a glycolipid fraction," Microbiology, vol. 144: p. 1247-1255.

Nicolson, et al., 1999, "Mycoplasmal infections in chronic illnesses," Medical Sentinel, vol. 4: p. 172-175, 191.

Ong et al., "Detection and widespread distribution of *Chlamydia pneumoniae* in the vascular system and its possible implications," J. Clin. Pathol. 49:102-106 (1996).

Palomino, et al., 2000, "Systematic mapping of hearts from chronic chagasic patients: the association between the occurrence of histopathological lesions and *Trypanosoma cruzi* antigens Annals of Tropical Medicine and Parasitology," vol. 94, No. 6: p. 571-579.

Parodi, et al., 1992, "Identification of the gene(s) coding for the trans-sialidase of *Trypanosome cruzi*" EMBO J., vol. 11: p. 1705-1710.

Pereira et al., "Lectin receptors as markers for *Trypanosoma cruzi*. Development stages and a study of the interaction of wheat germ agglutinin with sialic acid residues on epimastigotes cells," J. Exp. Med., 152:1375-1392 (1980).

Pereira et al., "The *Trypanosoma cruzi* neuraminidase contains sequences similiar to bacterial neuraminidases, YWTD repeats of the low density lipoprotein receptor, and Type III modules of fibronectin," J. Ex. Med. 174:179-191 (1991).

Pereira, 1983, "A developmentally regulated neuraminidase activity in *Trypanosoma cruzi*," Science, vol. 219: p. 1444-1446.

Perez, et al., 1997, "Leukocytoclastic vasculitis and polyarthritis associated with *Mycoplasma pneumoniae* infection," Clin. Infect. Dis., vol. 25: p. 154-155.

Pollevick, et al., 1991, "The complete sequence of a shed acute-phase antigen of *Trpanosoma cruzi*," Mol. Biochem. Parasitol., vol. 47: p. 247-250.

Razin et al. Eds., Molecular biology and pathogenicity of *Mycoplasmas*, Kluwer Academic/Plenum Publishers (New York, 2002) (Table of Contents Only).

Razin, et al., 1998, "Molecular biology and pathogenicity of *Mycoplasmas*," Microbiol. Mol. Biol. Rev., vol. 62, No. 4: p. 1094-1156.

Ribeirao, et al., 1997, "Temperature difference for trans-glycosylation and hydrolysis reaction reveal an acceptor binding site in the catalytic mechanism of *Trypanosoma cruzi* trans-sialidase," Glycobiology, vol. 7: p. 1237-1246.

Richards et al., "Prolactin is an antagonist of TGF-beta activity and promotes proliferation of murine B cell hybridomas," Cel. Immunol. 184: 85-91 (1998).

Roberts, et al., 1989, "Sialic Acid-dependent Adhesion of *Mycoplasma pneumoniae* to Purified Glycoproteins," Journal of Biological Chemistry, vol. 264: p. 9289-9293.

Rodrigues-Amaya, "Latin American food sources of carotenoids," Arch. Latinoam. Nutr. 49: 74S-84S (1999).

Ros-Bullon, et al., 1999, "Serum sialic acid in malignant melanoma patients: na ROC curve analysis," Anticancer Res., vol. 19, No. 4C: p. 3619-3622.

Sachse, et al., 1996, "Mechanisms and factors involved in *Mycoplasma bovis* adhesion to cells," Int. J. of Med. Microbiology, vol. 284: p. 80-92.

Sambiase, et al., 2000, "CMV and transplant-related coronary atherosclerosis: an immunohistochemical, in situ hybridization and polymerase chain reaction in situ study," Modern Pathology, vol. 13: p. 173-179.

Schenkman, et al., 1991, "Attachment of *Trypanosoma cruzi* trypomastigotes to receptors at restricted cell surface domains," Exp. Parasitol., vol. 72: p. 76-86.

Schenkman, et al., 1992, "*Trypanosoma cruzi* trans-sialidase and neuraminidase activities can be mediated by the same enzymes," J. Exp Med, vol. 175, No. 2: p. 567-575.

Schenkman, et al., 1994, "A proteolytic fragment of *Trypanosoma cruzi* trans-sialidase lacking the carboxy-terminal domain is active, monomeric, and generates antibodies that inhibit enzymatic activity," J. Biol. Chem., vol. 269: p. 7970-7975.

Schenkman, et al., 1994, "Structural and functional properties of Trypano-some trans-sialidase," Annu. Rev. Microbiol., vol. 48: p. 499-523.

Scudder, et al., 1993, "Enzymatic characterization of beta-D-galactoside alpha 2, 3-trans-sialidase from *Trypanosome cruzi*," J. Biol. Chem., vol. 268, No. 13: p. 9886-9891.

Sengupta A et al., "Administration of garlic and tomato can protect from carcinogen induced clastogenicity," Nutrit. Res. 22: 859-866 (2002).

Silva and Nussenzweig, 1953, "Sobre uma cepa de *Trypanosoma cruzi* altamente virulenta para o camundongo branco." Folia Clin Biol, vol. 20: p. 191-203.

Simecka, et al., 1992, "*Mycoplasmas* Diseases of Animals," in Maniloff et al. Eds., *Mycoplasmas*. Molecular Biology and Pathogenesis, American Society of Microbiology: p. 391-415.

Smith, et al., 1996, *Trypanosoma cruzi* trans-silaidase, Accession No. BAA09333, GI:840706, 964 aa.

Smith, et al., 1996, *Trypanosoma cruzi* trans-silaidase, Accession No. BAA09334, GI:840708, 1060 aa.

Sobeslaysky, et al., 1968, Adsorption of *Mycoplasma pneumonia* to neuraminic acid receptors of various cells and possible role in virulence by Journal of Bacteriology, p. 695-705.

Taylor-Robinson and Thomas, 1998, "*Chlamydia pneumoniae* in arteries: the facts, their interpretation, and future studies," J. Clin. Pathol., vol. 51: p. 793-797.

Taylor-Robinson, et al., 1981, "Mycoplasmal adherence with particular reference to the pathogenicity of *Mycoplasma pulmonis*," Isr. J. Med. Sci., vol. 17: p. 599-603.

Timms, "Vertex baldness link to prostate cancer," Lancet Oncology 3:584 (2002).

Treanor, et al., 2000, "Efficacy and Safety of the Oral Neuraminidase Inhibitor Oseltamivir in Treating Acute Influenza," JAMA, vol. 283.

Tsai, et al., 1995, "*Mycoplasmas* and onogenesis: persistent infection and multistage malignant transformation," Proc. Natl. Acad. Sci. U.S.A., vol. 92, No. 22: p. 10197-10201.

Uchide et al., "Effect of antioxidants on apoptosis induced by influenza virus infection: inhibition of viral gene replication and transcription with pyrrolidine dithiocarbamate," Antiviral Res. 56: 207-217 (2002).

Uemura et al., *Trypanosoma cruzi* trans-sialidase-neuraminidase, Accession No. S28409, GI:323067, 200 aa, Jan. 2000.

Uemura, et al., 1992, "Only some memeber of a gene family in *Trypanosome cruzi* encode proteins that express both trans-sialidase and neuraminidase," EMBO J., vol. 11: p. 3837-3844.

Uemura, et al., 1995, "*Trypanosoma cruzi* TCTS-121 gene for trans-sialidase," Accession No. D50685, GI:840707, 3183 bp.

Uemura, et al., 1995, "*Trypanosoma cruzi* TCTS-154 gene for trans-sialidase," Accession No. D50684, GI:840705, 2895 bp.

Umezawa, et al., 1996, "Immunobolt assay using excreted/secreted antigens of *Trypanosoma cruzi* in serodiagnosis of congenital, acute and chronic Chagas' disease," J. Clin. Microbiol., vol. 34: p. 2143-2147.

(56) References Cited

OTHER PUBLICATIONS

Umezawa, et al., 2001, "Enzyme-linked immunosorbent assay with *Trypanosoma cruzi* excreted-secreted antigens (TESA-ELISA) for serodiagnosis of acute and chronic Chagas' disease," Diag. Microbiol. Infect. Dis., vol. 39: p. 169-176.

Val'kovich, 1980, "Viral and *Mycoplasma*-induced glomerulopathies in children," Arkh. Pathol. 42(3):10-15. (Article is in the Russian language. English abstract is provided).

Vanderkerckhove, et al., 1992, "Substrate specificity of the *Trypanosoma cruzi* trans-sialidase," Glycobiology, vol. 2, No. 6: p. 541-548.

Walsmith et al., "Cachexia in rheumatoid arthritis," Int. J. Cardiol. 85: 89-99 (2002).

Wang et al., "The role of endotoxin, TNF-alpha, and IL-6 in inducing the state of growth hormone insensitivity," World J. Gastroenterol. 8: 531-536 (2002).

Watts, et al., 2003, "*Trypanosoma cruzi* trans-sialidase operates through a covalent sialyl-enzyme intermediate: Tryosine is the catalytic nucleophile," J. Am. Chem. Soc., vol. 125: p. 7532-7533.

Winther et al., "Effects of *Ginkgo biloba* extract on cognitive function and blood pressure in elderly subjects," Curr. Therap. Res. 59: 881-888 (1998).

Woese, et al., 1977, "Phylogenetic structure of the prokaryotic domain: the primary kingdoms," Proc. Natl. Acad. Sci. U.S.A., vol. 74: p. 5088-5090.

Woody et al., "Prolactin exerts hematopoietic growth-promoting effects in vivo and partially counteracts myelosuppression by azidothymidine," Exp. Hematol. 27: 811-816 (1999).

Zipes, et al., 2005, Braunwald's Heart Disease, Elsevier Saunders, Philadelphia (Table of Contents only).

U.S. Appl. No. 13/304,109, filed Nov. 23, 2011.

Kornsulee Ratanapariyanuch's Thesis Abstract (submitted to the University of Saskatchewan library on Apr. 13, 2009).

U.S. Appl. No. 13/304,109, Oct. 1, 2012 Response to Non-Final Office Action.

FIGURE 2
SEQ. ID. NO. 3

```
ATGGGCAGCA GCCATCATCA TCATCATCAC AGCAGCGGCC TGGTGCCGCG CGGCAGCCAT   60
Atggcacccg gatcgagccg agttgagctg tttaagcggc aaagctcgaa ggtgccattt  120
gaaaagggcg gcaaagtcac cgagcgggtt gtccactcgt tccgcctccc cgcccttgtt  180
aatgtggacg gggtgatggt tgccatcgcg gacgctcgct acgaaacatc caatgacaac  240
tccctcattg atacggtggc gaagtacagc gtggacgatg gggagacgtg ggagacccaa  300
attgccatca agaacagtcg tgcatcgtct gtttctcgtg tggtggatcc cacagtgatt  360
gtgaagggca acaagcttta cgtcctggtt ggaagctaca acagttcgag gagctactgg  420
acgtcgcatg gtgatgcgag agactgggat attctgcttg ccgttggtga ggtcacgaag  480
tccactgcgg gcggcaagat aactgcgagt atcaaatggg ggagccccgt gtcactgaag  540
gaattttttcc cggcggaaat ggaaggaatg cacacaaatc aatttcttgg cggtgcaggt  600
gttgccattg tggcgtccaa cgggaatctt gtgtaccctg tgcaggttac gaacaaaaag  660
aagcaagttt tttccaagat cttctactcg gaagacgagg gcaagacgtg gaagtttggg  720
gagggtagga gtgattttgg ctgctctgaa cctgtggccc ttgagtggga ggggaagctc  780
atcataaaca ctcgagttga ctatcgccgc cgtctggtgt acgagtccag tgacatgggg  840
aattcgtggg tggaggctgt cggcacgctc tcacgtgtgt ggggcccctc accaaaatcg  900
aaccagcccg gcagtcagag cagcttcact gccgtgacca tcgagggaat gcgtgttatg  960
ctcttcacac acccgctgaa ttttaaggga aggtggctgc gcgaccgact gaacctctgg 1020
ctgacggata accagcgcat ttataacgtt gggcaagtat ccattggtga tgaaaattcc 1080
gcctacagct ccgtcctgta caaggatgat aagctgtact gtttgcatga gatcaacagt 1140
aacgaggtgt acagccttgt ttttgcgcgc ctggttggcg agctacggat cattaaatca 1200
gtgctgcagt cctggaagaa ttgggacagc cacctgtcca gcatttgcac ccctgctgat 1260
ccagccgctt cgtcgtcaga gcgtggttgt ggtcccgctg tcaccacggt tggtcttgtt 1320
ggcttttttgt cgcacagtgc caccaaaacc gaatgggagg atgcgtaccg ctgcgtcaac 1380
gcaagcacgg caaatgcgga gagggttccg aacggtttga gtttgcgggg gttggcgga 1440
ggggcgcttt ggccggtgag ccagcagggg cagaatcaac ggtatcactt tgcaaaccac 1500
gcgttcacgc tggtggcgtc ggtgacgatt cacgaggttc cgagcgtcgc gagtcctttg 1560
ctgggtgcga gcctggactc ttctggtggc aaaaaactcc tggggctctc gtacgacgag 1620
aagcaccagt ggcagccaat atacggatca acgccggtga cgccgaccgg atcgtgggag 1680
atgggtaaga ggtaccacgt ggttcttacg atggcgaata aaattggttc ggtgtacatt 1740
gatggagaac tctggagggg ttcagggcag accgttgtgc cagacgggag gacgcctgac 1800
atctcccact tctacgttgg cgggtatgga aggagtgata tgccaaccat aagccacgtg 1860
acggtgaata atgttcttct ttacaaccgt cagctgaatg ccgaggagat caggaccttg 1920
ttcttgagcc aggacctgat tggcacggaa gcacacatgg gcagcagcag cggcagcagt 1980
gaaagaagta cgcccGGATC CGGCTGCTAA                                  2010
```

FIG. 3A
SEQ. ID. NO. 4

| | | | | | | | | | | | | | | | | | | | | |
|---|---|---|---|---|---|---|---|---|---|---|---|---|---|---|---|---|---|---|---|---|
| Met<br>1 | Gly | Ser | Ser | His<br>5 | His | His | His | His | His<br>10 | His | Ser | Ser | Gly | Leu<br>15 | Val | Pro | Arg | Gly | Ser<br>20 | His |
| Met | Ala | Pro | Gly | Ser<br>25 | Ser | Lys | Phe | Leu | Leu<br>30 | Val | Arg | Lys | Ala | Ser<br>35 | Gly | Ala | Val | Ile | Phe<br>40 | |
| Glu | Lys | Gly | Asp | Lys<br>45 | Val | Thr | Glu | Gln | Val<br>50 | Phe | Arg | Pro | Ala | Arg<br>55 | Ala | Asn | Leu | Val | Val<br>60 | |
| Asn | Val | Asp | Gly | Val<br>65 | Met | Val | Ala | Ala | Ala<br>70 | Val | Asp | Ile | Tyr | Glu<br>75 | Thr | Asn | Asp | Thr | Asn<br>80 | |
| Ser | Leu | Ile | Asp | Thr<br>85 | Val | Ala | Lys | Ala | Ser<br>90 | Tyr | Gly | Tyr | Ser | Glu<br>95 | Thr | Glu | Glu | Thr | Gln<br>100 | |
| Ile | Ala | Ile | Lys | Asn<br>105 | Ser | Arg | Ala | Ala | Val<br>110 | Ser | Val | Asp | Arg | Val<br>115 | Asp | Arg | Ser | Val | Ile<br>120 | |
| Val | Lys | Gly | Asn | Lys<br>125 | Leu | Tyr | Val | Leu | Val<br>130 | Gly | Leu | Asn | Tyr | Ser<br>135 | Ala | Glu | Val | Ser | Trp<br>140 | |
| Thr | Ser | His | Gly | Asp<br>145 | Ala | Arg | Asp | Trp | Ala<br>150 | Ile | Leu | Ala | Leu | Val<br>155 | Ile | Val | Val | Thr | Lys<br>160 | |
| Ser | Thr | Ala | Gly | Gly<br>165 | Lys | Ile | Thr | Ala | Ser<br>170 | Ile | Lys | Trp | Gly | Pro<br>175 | Ser | Pro | Val | Ser | Lys<br>180 | |
| Glu | Phe | Phe | Pro | Ala<br>185 | Glu | Met | Glu | Gly | Met<br>190 | His | Thr | Asn | Asp | Phe<br>195 | Leu | Val | Gly | Ala | Gly<br>200 | |
| Val | Ala | Ile | Val | Ala<br>205 | Ser | Asn | Gly | Phe | Leu<br>210 | Val | Gly | Tyr | Pro | Gln<br>215 | Val | Thr | Asn | Lys | Lys<br>220 | |
| Lys | Gln | Val | Phe | Ser<br>225 | Lys | Ile | Phe | Tyr | Ser<br>230 | Glu | Asp | Phe | Gly | Lys<br>235 | Thr | Trp | Lys | Phe | Gly<br>240 | |
| Glu | Gly | Arg | Ser | Asp<br>245 | Phe | Gly | Cys | Ser | Glu<br>250 | Glu | Pro | Gly | Ala | Glu<br>255 | Trp | Glu | Gly | Lys | Leu<br>260 | |
| Ile | Ile | Asn | Thr | Arg<br>265 | Asp | Tyr | Arg | Ala | Arg<br>270 | Val | Tyr | Arg | Val | Glu<br>275 | Ser | Ser | Asp | Met | Gly<br>280 | |
| Asn | Ser | Trp | Val | Glu | Ala | Gly | Thr | Leu | Ser | Arg | Val | Val | Trp | Gly | Pro | Ser | Pro | Lys | Ser | |

FIG. 3B

|   |   |   |   | 285 |   |   |   |   | 290 |   |   |   |   | 295 |   |   |   |   | 300 |
|---|---|---|---|---|---|---|---|---|---|---|---|---|---|---|---|---|---|---|---|
| Asn | Gln | Pro | Gly | Ser 305 | Gln | Ser | Phe | Ala | Val 310 | Thr | Ile | Glu | Gly | Met 315 | Arg | Val | Met | Val | Met 320 |
| Leu | Phe | Thr | His | Pro 325 | Leu | Asn | Phe | Lys | Trp 330 | Leu | Arg | Asn | Leu | Asp 335 | Arg | Leu | Asn | Leu | Trp 340 |
| Leu | Thr | Asp | Asn | Gln 345 | Arg | Ile | Tyr | Phe | Val 350 | Gln | Gly | Ser | Asp | Ile 355 | Gly | Asp | Glu | Asn | Ser 360 |
| Ala | Tyr | Ser | Ser | Val 365 | Leu | Tyr | Lys | Leu | Asp 370 | Leu | Lys | Tyr | Cys | Leu 375 | His | Glu | Ile | Asn | Ser 380 |
| Asn | Glu | Val | Tyr | Ser 385 | Leu | Val | Phe | Ala | Arg 390 | Val | Leu | Gly | Glu | Leu 395 | Arg | Ile | Ile | Lys | Ser 400 |
| Val | Leu | Gln | Ser | Ser 405 | Lys | Asn | Trp | Asp | Ser 410 | His | Leu | Ser | Ser | Ile 415 | Cys | Thr | Pro | Ala | Asp 420 |
| Pro | Ala | Ala | Ser | Ser 425 | Ser | Glu | Arg | Gly | Cys 430 | Gly | Pro | Ala | Val | Thr 435 | Thr | Val | Cys | Leu | Val 440 |
| Gly | Phe | Leu | Ser | His 445 | Ala | Ala | Thr | Lys | Thr 450 | Glu | Trp | Ser | Asp | Ala 455 | Tyr | Arg | Gly | Val | Asn 460 |
| Ala | Ser | Thr | Ala | Asn 465 | Val | Glu | Arg | Val | Pro 470 | Leu | Gly | Ala | Asp | Phe 475 | Ala | Gly | Val | Gly | Gly 480 |
| Gly | Ala | Leu | Trp | Pro 485 | Ser | Gln | Gln | Lys | Gly 490 | Gln | Lys | Arg | Lys | Tyr 495 | His | Phe | Ala | Asn | His 500 |
| Ala | Phe | Thr | Leu | Val 505 | Ala | Val | Gln | Val | Ile 510 | His | Leu | Pro | Pro | Ser 515 | Val | Ala | Ser | Pro | Leu 520 |
| Leu | Gly | Ala | Ser | Leu 525 | Asp | Ser | Thr | Leu | Gly 530 | Lys | Leu | Lys | Leu | Gly 535 | Leu | Ser | Tyr | Asp | Glu 540 |
| Lys | His | Gln | Trp | Gln 545 | Glu | Ile | Tyr | Thr | Ser 550 | Pro | Thr | Thr | Ser | Pro 555 | Thr | Gly | Ser | Trp | Glu 560 |
| Met | Gly | Lys | Arg | Tyr 565 | His | Val | Val | Leu | Thr 570 | Met | Lys | Lys | Asn | Ile 575 | Gly | Ser | Val | Tyr | Ile 580 |
| Asp | Gly | Glu | Pro | Leu 585 | Glu | Gly | Ser | Gly | Gln 590 | Thr | Pro | Val | Asn | Asp 595 | Gly | Arg | Thr | Pro | Asp 600 |
| Ile | Ser | His | Phe | Tyr | Val | Gly | Tyr | Tyr | Gly | Gly | Ser | Arg | Met | Pro | Thr | Ile | Ser | His | Val |

FIG. 3C

|     |     |     | 605 |     |     |     |     |     | 610 |     |     |     |     | 615 |     |     |     | 620 |
|-----|-----|-----|-----|-----|-----|-----|-----|-----|-----|-----|-----|-----|-----|-----|-----|-----|-----|-----|
| Thr | Val | Asn | Val | Leu | Leu | Tyr | Asn | Arg | Gln | Leu | Asn | Ala | Glu | Ile | Arg | Thr | Leu |
|     |     |     | 625 |     |     |     |     |     | 630 |     |     |     |     | 635 |     |     |     | 640 |
| Phe | Leu | Ser | Gln | Leu | Ile | Gly | Thr | Glu | Ala | His | Met | Gly | Ser | Ser | Ser | Gly | Ser |
|     |     |     | 645 |     |     |     |     |     | 650 |     |     |     |     | 655 |     |     |     | 660 |
| Glu | Arg | Ser | Thr | Gly | Ser | Gly | Cys |
|     |     |     | 665 |

DIAGNOSIS, PREVENTION AND TREATMENT OF DISORDERS CHARACTERIZED BY UNDESIRABLE CELL PROLIFERATION

PRIORITY CLAIM

This application is a continuation in part of U.S. Ser. No. 12/770,487, filed Apr. 29, 2010, and issued as U.S. Pat. No. 7,914,781 on Mar. 29, 2011, which is a divisional of U.S. Ser. No. 12/033,193, filed Feb. 19, 2008, and issued as U.S. Pat. No. 7,732,410 on Jun. 8, 2010, which is a continuation in part of U.S. Ser. No. 10/952,003, filed Sep. 28, 2004, and issued as U.S. Pat. No. 7,335,638 on Feb. 26, 2008, which is a continuation in part of International Patent Application No. PCT/BR03/0049, filed Mar. 28, 2003 and published in English on Oct. 9, 2003 as WO 03/082324, and further claims priority to U.S. Provisional Application Ser. No. 60/890,977, filed Feb. 21, 2007, all of which are incorporated by reference in their entireties herein.

1. INTRODUCTION

The present invention relates to compositions and methods for the reduction of atherosclerotic plaques and the decrease in the level of total serum cholesterol, triglycerides, serum LDL cholesterol, and serum HDL cholesterol. The present invention also relates to methods for the diagnosis, prevention and treatment of disorders characterized by undesirable cell proliferation, such as atherosclerosis and mycoplasma associated diseases.

2. BACKGROUND

Current treatment for atherosclerosis involves lipid-lowering medications and drugs that affect lipid metabolism, including statins, bile acid absorption inhibitors, cholesterol absorption inhibitors, fibrates and antioxidants such as probucol, among others. (Zipes et al. Eds., 2005, Braunwald's Heart Disease, Elsevier Saunders, Philadelphia). These treatment regimens are based, at least in part, on the theory that oxidized lipoproteins are the main causative factor of atherosclerosis. However, the exact mechanism by which cholesterol oxidizes is still not fully understood.

Archaea are the most ancient microorganisms existing in nature, but have been characterized only recently. See, Woese et al., Proc Natl. Acad. Sci. U.S.A. 74: 5088-5090 (1977). They inhabit extreme environments and are constituted by lipid monolayer membranes. Rich alkaline atmosphere with sodium ions and metals prevents proliferation of other bacteria, but is favorable to archaea's growth. Archaea have been isolated from alkaline waters from the Dead Sea, the Great Salt Lake and Yellowstone National Park. They have a small size, can—just barely—be viewed with an optical microscope, and observation of structural details requires electron microscopy. See, Howland et al., The surprising archaea. Discovering another domain of life, Oxford University Press (New York, 2000). Some are considered hyperthermophilic as they survive in very high temperatures.

Another unusual characteristic of some archaea is that they appear to use metal as an energy source. See, Amend et al., F.E.M.S. Microbiol. Rev. 25: 175-243 (2001). It is considered that archaea usually need an anaerobic or nearly anaerobic environments to carry out oxidation-reduction reactions with participation of different chemical compounds, including metals.

Recently, a new kind of extremely small archaea, which is dependent on bigger archaea, was described and named nanoarchaea. See, Huber J et al., Nature 417: 63-67 (2002). With the exception of archaea that reside in the mammalian intestine and produce methane gases, there is no report of archaea existing within plants or animals. See, Florin T H J et al., Am. J. Gastroenterol. 95: 2872-2879 (2000).

3. SUMMARY OF THE INVENTION

The present invention relates to compositions and methods for the reduction of atherosclerotic plaques. Without being limited by theory, it is based on the hypothesis that the presence of mycoplasma and one or more other microorganism promotes atheroma formation. The compositions and methods of the invention may also be used to decrease the level of total serum cholesterol, triglycerides, serum LDL cholesterol, and serum HDL cholesterol. In one non-limiting embodiment of the invention, the composition comprises an agent that removes sialic acid residues, a metal chelator, and optionally one or more purified plant extracts.

In a preferred non-limiting embodiment of the invention, the composition comprises a protein capable of removing sialic acid residues, such as a neuraminidase enzyme and/or a trans-sialidase enzyme; a metal chelator, preferably pyrrolidine dithiocarbamate (PDTC), along with one or more purified plant extracts. The purified plant extract may be derived from a plant selected from the group consisting of *Allium sativum* (garlic), *Ginkgo biloba*, tomato, orchids of the genus *Cymbidium* and *Dendrobium*, for example, *Cymbidium* ssp, *Dendrobium nobile* and *Dendrobium moschatum*; guava, ginseng, for example, *Pfaffia paniculata* (Brazilian ginseng); *Zingiber officinale* (ginger), and tobacco, wherein the purified extract comprises particles containing DNA or RNA, such as an archaea or a nanoarchaea.

The present invention also provides methods for increasing the number of non-pathogenic archaea in a plant extract, while also decreasing the number of pathogenic archaea in the plant extract. In one embodiment, the non-pathogenic archaea in a plant extract are increased and the pathogenic archaea in the plant extract are decreased by aging the plant extract, and then diluting the plant extract with thermal water, followed by an additional aging period.

The present invention also provides for methods for the diagnosis, prevention and treatment of disorders characterized by undesirable cell proliferation, for example, atherosclerosis and mycoplasma associated diseases. In one embodiment, such diagnosis includes detecting mycoplasma or mycoplasma lipoprotein in the serum or an atherosclerotic lesion of a patient. In other embodiments, diagnosis includes detecting chlamydia or chlamydia lipopolysaccharide (LPS) in the serum or an atherosclerotic lesion of a patient. In other embodiments, diagnosis includes detecting pathogenic archaea in the serum or an atherosclerotic lesion of a patient. In other embodiments, diagnosis includes detecting C reactive protein (CRP) in the serum or an atherosclerotic lesion of a patient.

4. BRIEF DESCRIPTION OF THE FIGURES

FIG. 1A-J. (A-E) shows macroscopic aortic atheroma plaques (arrows) and (F-J) shows *Chlamydia pneumoniae* positive antigen expression in aortal intimal areas (arrows) of rabbits fed a 1% cholesterol diet and submitted to different anti-atherosclerotic treatments. Group II (A, F) received no treatment, Group III (B, G) was treated with trans-sialidase ("TS")+pyrrolidine dithiocarbamate ("PDTC"), Group IV (C, H) was treated with TS+PDTC+*Allium sativum* ("AS"), Group V (D, I) was treated with TS+PDTC+AS+*Ginko biloba* ("GB"), and Group VI (E, J) was treated with TS+PDTC+AS+GB+*Zingiber officinale* ("ZO").

FIG. 2 shows the nucleotide sequence of a plasmid encoding the catalytic trans-sialidase unit of trans-sialidase from *Trypanosoma cruzi* (SEQ ID NO:3). The letters in capital represent the pET14b plasmid and the underlined letters correspond to the position of the oligonucleotides used to amplify the *Trypanosoma cruzi* clone.

FIG. 3A-C shows the amino acid sequence of the protein encoded by the nucleic acid sequence depicted in FIG. 2. (SEQ ID NO:4). In bold are the amino acids not found in the original clone.

Figure 7:
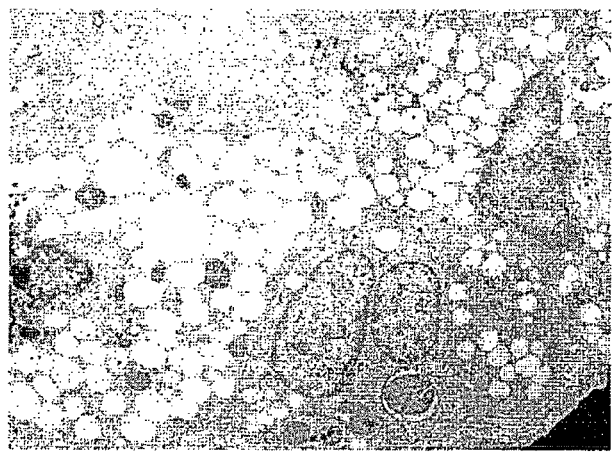

FIG. 7 shows an electron micrograph of a human aortic aneurysm. The aortic aneurysm exhibits many round lipidic bodies in both the cytoplasm of macrophages and in the extracellular matrix. The round lipidic bodies are surrounded by immunogenic lymphocytes.

Figure 8:

FIG. 8 shows a high magnification view of the round lipidic body described in FIG. 7. The round lipidic body exhibits a clear external membrane corresponding to the morphology of the large lipidic archaea microbes shown in FIGS. 5 and 6 (and also isolated from tobacco).

Figure 9:
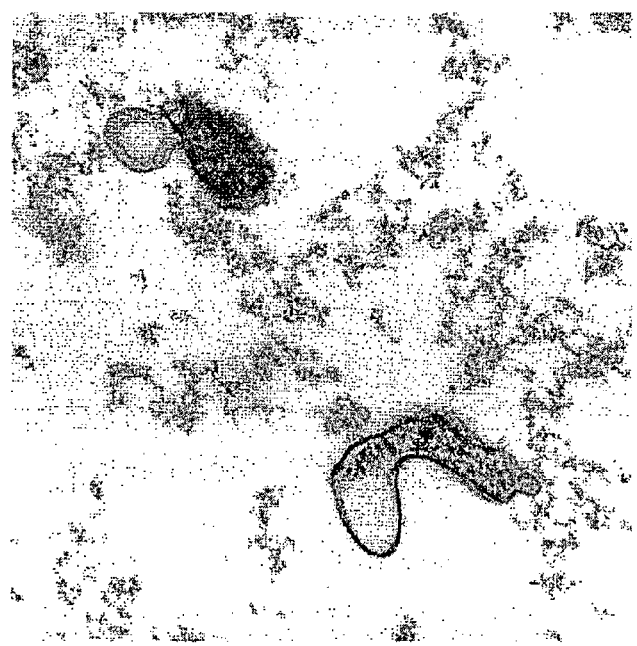

FIG. 9 shows an electron micrograph of the serum of a patient with symptoms of Lyme disease, but negative for *Borrelia burgdorferi*, showing two mycoplasmas that have one envoltory membrane and granulous electron dense material inside. On the top the mycoplasma in intimal contact with a structure with morphology of archaea characterized by thin delicate envoltory lipidic monolayer membrane and having an internal empty space, which is characteristic of the archaea present in tissue lesions.

SEQUENCE LISTING

The specification further incorporates by reference the Sequence Listing submitted herewith via EFS on Jul. 11, 2011. Pursuant to 37 C.F.R. §1.52(e)(5), the Sequence Listing text file, identified as 0685280115seqlist.txt, is 9,532 bytes and was created on Jun. 29, 2011. The Sequence Listing, electronically filed herewith, does not extend beyond the scope of the specification and thus does not contain new matter.

5. DETAILED DESCRIPTION OF THE INVENTION

For purposes of clarity, and not by way of limitation, the detailed description of the invention is divided into the following subsections:
(i) compositions for treating atherosclerosis; and
(ii) therapeutic uses.

5.1 Compositions for Treating Atherosclerosis

The present invention provides for compositions and methods that prevent or treat diseases associated with undesirable cell proliferation and fibrosis. Specifically, the compositions and methods of the invention inhibit the narrowing of blood vessels and reduce atherosclerosis. The compositions and methods of the present invention also decrease the level of total serum cholesterol as well as serum LDL, serum HDL and triglyceride levels in a treated patient.

In particular embodiments of the invention, the composition comprises a protein capable of removing sialic acid residues, wherein removal of the sialic acid residues inhibits or prevents the attachment of a mycoplasma and one or more non-mycoplasma microorganism to a host cell. Preferred non-limiting embodiments further comprise a metal chelator and/or one or more purified plant extracts. Administration of the compounds of the invention has the effect of reducing the presence of atherosclerotic plaques on a blood vessel, and decreasing the level of blood serum lipids, total serum cholesterol, serum LDL, serum HDL, and triglycerides of a treated individual.

The term "composition" as used herein means agents or mixtures or combinations thereof effective to prevent or reduce the rate of growth of an atherosclerotic lesion and/or to decrease the presence of a mycoplasma and non-mycoplasma microorganism with an atherosclerotic plaque. In one embodiment, the composition inhibits the ability of the mycoplasma and non-mycoplasma to associate with a substrate, for example, but not limited to, a blood vessel. In another non-limiting embodiment, the composition inhibits the association of a mycoplasma and a non-mycoplasma microorganism.

The term "atherosclerosis," "atherosclerotic plaque," "plaque," or "atheroma" as used herein refers to the accumulation of one or more of lipids, cholesterol, collagen, and macrophages on the walls of a subject's blood vessel. The presence of plaques in a blood vessel can also be associated with ossification and calcification of the blood vessel walls.

The term "blood serum lipids" as used herein refers to HDL and LDL lipoproteins.

The term "HDL" as used herein means high density lipoprotein.

The term "LDL" as used herein means low density lipoprotein.

In further non-limiting embodiments of the invention, the mycoplasma may be *Mycoplasma (M.) buccale, M. faucium, M. fermentans, M. genitalium, M. hominis, M. lipophilum, M. oral, M. penetrans, M. pneumoniae, M. salivarium,* or *M. spermatophilum,* wherein the mycoplasma is associated with one or more additional non-mycoplasma microorganisms. The one or more additional non-mycoplasma microorganism may be a bacteria, archaea or virus, for example, but not limited to, spirochete or chlamydia such as *Chlamydia pneumoniae*. According to the invention, the mycoplasma and non-mycoplasma may be attached to a substrate, for example, but not limited to, a blood vessel or an atherosclerotic plaque. In a further non-limiting embodiment, the mycoplasma and non-mycoplasma are attached to the substrate by sialic acid.

In a preferred embodiment of the invention, the protein capable of removing sialic acid residues is a trans-sialidase or neuraminidase enzyme A combination of such enzymes or an enzyme having both activities may also be used.

In certain non-limiting embodiments, the composition comprises a neuraminidase enzyme of, for example but not limited to, *Bacteroides fragilis, Streptococcus pneumoniae, Streptococcus oralis, Arthrobacter ureafaciens, Clostridium perfringens, Mycoplasma alligatoris, Arcanobacterium pyogenes, Clostridium sordellii, Pseudomonas aeruginosa, Micromonospora viridifaciens, Vibrio cholerae. Streptomyces avermitilis,* Influenza virus, *Streptomyces coelicolor, Flavobacteriales bacterium,* and *Solibacter usitatus*.

In other non limiting embodiments, the protein is a trans-sialidase, for example, the trans-sialidase enzyme of *Trypanosoma brucei*.

In a preferred embodiment, the composition is the trans-sialidase enzyme of *Trypanosoma cruzi*, or a portion or variant of the native enzyme which has trans-sialidase activity.

Alternatively, the trans-sialidase enzyme can be a recombinant trans-sialidase enzyme.

In specific non-limiting embodiments, the recombinant trans-sialidase is as described in International Patent Publication WO 2002/002050 by Higuchi et al., published Jan. 10, 2002; and U.S. Pat. No. 7,108,851 by Higuchi et al., issued Sep. 19, 2006. For example, the trans-sialidase gene may be obtained from a genomic clone, isolated from a commercially available lambda Zap® II library (Stratagene, http://www.stratagene.com) of *T. cruzi* Y strain (Silva and Nussenzweig, 1953, Folia Clin Biol 20: 191-203), as described in Uemura et al. (Uemura et al., 1992, EMBO J 11: 3837-3844). From the original lambda clone, which expresses enzymatic activity, an SK plasmid containing the trans-sialidase gene may be generated (SK-154-0). The preferred plasmid used is pTSII, which corresponds to a fragment of the original gene (clone 154-0) amplified through PCR, and inserted into the sites NdeI and BamHI of the vector pET14b (Novagen—http://www.novagen.com). The PCR product may be amplified using SK-154-0 as a template with the following primers:

```
                                                 (SEQ ID NO: 1)
a) TSPET14: 5'-GGAATTCCATATGGCACCCGGATCGAGC (SEQ ID NO: 2)
b) RT154: 5'-CGGATCCGGGCGTACTTCTTTCACTGGTGCCGGT
```

The resulting PCR product should have a nucleic acid sequence as set forth in FIG. 2 (SEQ ID NO:3), and a corresponding amino acid sequence as depicted in FIG. 3 (SEQ ID NO:4). The resulting plasmid may be transformed into the *Escherichia coli* BLB21 DE3. The construct can be made in two steps due to an internal BamHI site in the trans-sialidase gene. The PCR product may be treated with BamHI and NdeI enzymes, and the resulting fragments fractionated by electrophoresis on an agarose gel. The separated fractions may then be purified from the gel with the Sephaglass purification kit (Amersham-Pharmacia). The 5' NdeI-BamHI digestion fragment may be ligated into the pET14b vector which has been pre-digested with BamHI and NdeI. The ligation products may be used to transform K12 DH5a *E. coli* cells. The plasmid containing *E. coli* cells may be selected and the plasmid purified by methods known in the art. The purified construct may be treated with BamHI, shrimp alkaline phosphatase, and ligated with the BamHI-BamHI-3' fragment purified from the fractionation gel. The ligation products may then be used to transform K12 DH5a *E. coli* cells, from which clones expression of trans-sialidase may be selected and purified. The final plasmid may be confirmed by restriction analysis and used to transform the BLB21 DE3 pLys strain of *E. coli*, from which recombinant trans-sialidase enzyme can be purified, as described in International Patent Publication WO/2002/002050 by Higuchi et al., published Jan. 10, 2002; and U.S. Pat. No. 7,108,851 by Higuchi et al., issued Sep. 19, 2006.

Alternatively, the trans-sialidase enzyme may be purified from a culture of *Trypanosoma cruzi*, such as, for example, a culture according to Kloetzel et al. (Kloetzel et al., 1984, Rev. Inst. Med. Trop. Sao Paulo., 26:179-85). Supernatant from the culture may be filtered through a 1 μm pore filter in a vacuum chamber. The enzyme may be further purified by filtering the supernatant through a 0.22 μm filter and then precipitating the filtrate with a 50% $(NH_4)_2SO_4$ solution. The precipitates may then be dialyzed against phosphate-buffered saline, and passed through a tresyl-agarose column comprising an immobilized anti-trans-sialidase monoclonal or polyclonal antibody. The column may be washed with phosphate-buffered saline, followed by an additional wash with 10 mM sodium phosphate, pH 6.5. The trans-sialidase may then be eluted with a 3.5 mM $MgCl_2$, 10 mM sodium phosphate, pH 6.0 solution. The fractions eluted from the column may be filtered through a Sephadex G-25 column equilibrated with 20 mM Tris-HCl, pH 8.0, to remove the $MgCl_2$. The trans-sialidase may be further purified by passage through a Mono Q column equilibrated in 20 mM Tris-HCl, pH 8.0, and eluted with a linear gradient from 0 to 1 mM NaCl in the same buffer.

The purified enzyme derived from the culture should comprise 400 kDa multimeric aggregates. The enzymatic activity of the purified trans-sialidase may be measured according to methods described in International Patent Publication WO 2002/002050 by Higuchi et al., published Jan. 10, 2002; and U.S. Pat. No. 7,108,851 by Higuchi et al., issued Sep. 19, 2006.

In non-limiting embodiments, the purified trans-sialidase has an enzymatic activity of between 0.1 and 10 U/ml, more preferably between 1.0 and 5.0 U/ml, and most preferably 1.3 U/ml.

In certain non-limiting embodiments, the composition comprises a metal chelator, for example, but not limited to, Nitrilotriacetate (NTA), diphenylthiocarbazone(dithizone), histidine, the lipophilic metal chelator DP-109, ethylene glycol tetraacetic acid (EGTA), ethylenediaminetetraacetic acid (EDTA), DMPS (2,3-dimercapto-1-propanesulfonate), Lysinoalanine, Synthetic lysinoalanine (N-ε-DL-(2-amino-2-carboxyethyl)-L-lysine), tetracycline, alpha lipoic acid (ALA), Dimercaptosuccinic acid, (DMSA), 2,3-Dimercapto-1-propanesulfonic acid (DMPS), Calcium disodium versante $(CaNa_2$-EDTA), D-penicillamine, Deferoxamine, Defarasirox, Dimercaprol (BAL), the calcium salt of diethylene triamine pentaacetic acid (DTPA), or any other metal chelator known in the art. In a preferred non-limiting embodiment, the metal chelator is pyrrolidine dithiocarbamate (PDTC). The composition of the invention may comprise the metal chelator in a concentration of between about 0.01 and 10 mg/ml, more preferably between about 0.5 and 5 mg/ml, more preferably between about 1 and 2 mg/ml, and most preferably about 1.5 mg/ml.

In a further non-limiting embodiments, the plant extract may be derived from, for example but not limited to, *Allium sativum* (garlic), *Ginkgo biloba*, tomato, orchid, guava, ginseng, for example *Pfaffia paniculata* (Brazilian ginseng); *Zingiber officinale* (ginger); or tobacco, wherein the orchid is preferably of the genus *Cymbidium*, for example, yellow or green orchids from the genus *Cymbidium* (*Cymbidium* ssp). Alternatively, the orchid may be of the genus *Dendrobium*, for example, *Dendrobium nobile* or *Dendrobium moschatum*.

The extract from plants may be obtained by adding a solvent, such as, for example, alcohol, to the plant tissue, for example, but not limited to, roots, cloves, flower petals, or leaves which may be chopped, or macerated prior to mixture with the solvent. The solvent may be mixed with the plant tissue in a proportion of between 1:99 and 60:40, more preferably between 15:85 and 50:50 and most preferably between 30-40:70-60 of plant mass:alcohol. The solvent can be an alcohol, for example, ethanol, methanol, or grain alcohol, and can have a concentration of between 60% and 100%, more preferably between 70% and 95%, and most preferably 92% alcohol. The plant/alcohol mixture may be aged in a dark, anaerobic environment for a period of time between 15 days and 24 months, more preferably between 1 and 15 months, and most preferably 12 months.

According to the invention, the extract derived from plant comprises particles containing nucleic acid (DNA or RNA), wherein the particle is an archaea (preferably non-pathogenic) and/or a nanoarchaea, and further wherein the particle is present in an amount effective to prevent or inhibit the growth of a mycoplasma and one or more non-mycoplasma microorganisms. Aging of the plant/alcohol mixture increases the concentration of particles in the mixture.

The plant/alcohol mixture may be purified, and the concentration of nanoparticles may be increased through one or more filtrations. The mixture may be filtered through pores of between 0.5 μm and 50 μm, more preferably between 5 μm and 20 μm, and most preferably 11 μm, for example, but not limited to Whatman qualitative filter paper grade 1, diameter 24 cm, pore size 11 μM. Vacuum chambers can also be used separately, or in addition to other filtration methods. Additionally, glass microfiber filters may be used for filtration, for example, but not limited to, a 47 mm diameter glass microfiber filter with a pore size of 1.1 μm. Any filtration methods known in the art may be used to filter the aged plant/alcohol mixture.

In a non-limiting embodiment, the plant/alcohol mixture can be subjected to additional aging during the filtration process. For example, olive oil may be added to the filtrate to create a 1% olive oil filtrate mixture, followed by an additional month of storage in a dark anaerobic environment.

According to the methods of the present invention, aging a plant extract increases the proportion of non-pathogenic archaea to pathogenic archaea in the plant extract.

In one embodiment, aging the plant extract increases the number of non-pathogenic archaea in the plant extract.

In another embodiment, aging the plant extract decreases the number of pathogenic archaea in the plant extract.

In another embodiment, an aged plant extract, or alternatively, a plant extract that has not been aged, can be diluted with a dilutant and aged for an additional period of time.

In a further non-limiting embodiment, the dilutant can be thermal water, oil, for example, olive oil, or any other dilutant known in the art.

In another non-limiting embodiment, the plant extract or the diluted plant extract can be aged for between 15 days and 24 months.

In another non-limiting embodiment, the plant extract or the diluted plant extract, can be aged for 30 days.

Furthermore, the composition may comprise particles and/or nanoparticles containing DNA or RNA, wherein the particles are a non-pathogenic archaea and/or a nanoarchaea, and further wherein the particle is present in amounts effective to prevent or inhibit the growth of a mycoplasma and one or more non-mycoplasma microorganisms. The nanoparticles may be between 5-500 nm, more preferably between 15-250 nm, and most preferably between 30-150 nm in diameter. Alternatively, the composition may comprise medium particles of between 500 nm and 1.1 μm in diameter. Additionally, the compositions may comprise one or a combination of both small and medium particles. The size of a particle can enlarge or decrease depending on the concentration of water and ions in a solution comprising the particles, such as, for example, Na+ or Ca+.

Figure 4:
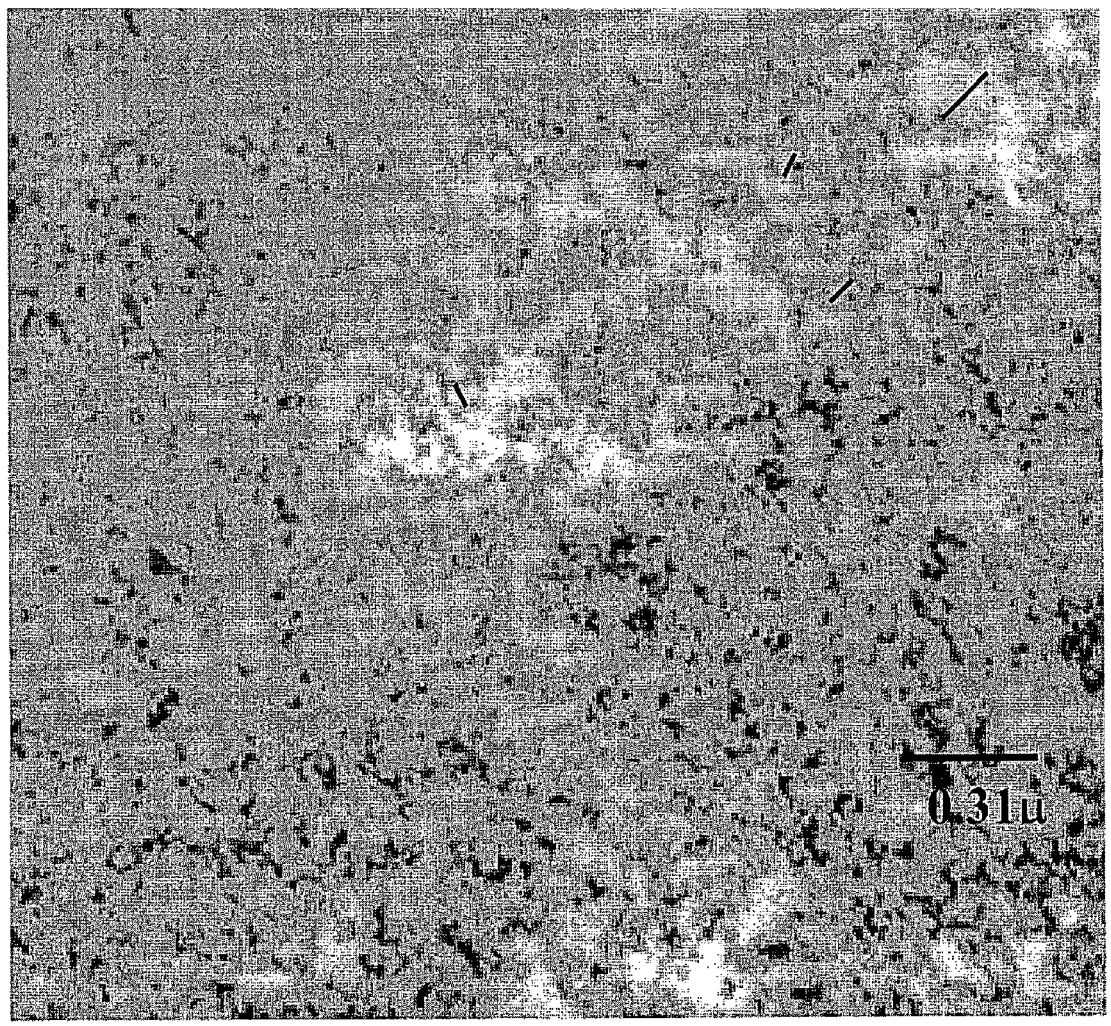
FIG. 4 shows small dark electron-dense nanoarchaea of between 0.03-0.15 µm in diameter.
Figure 5:
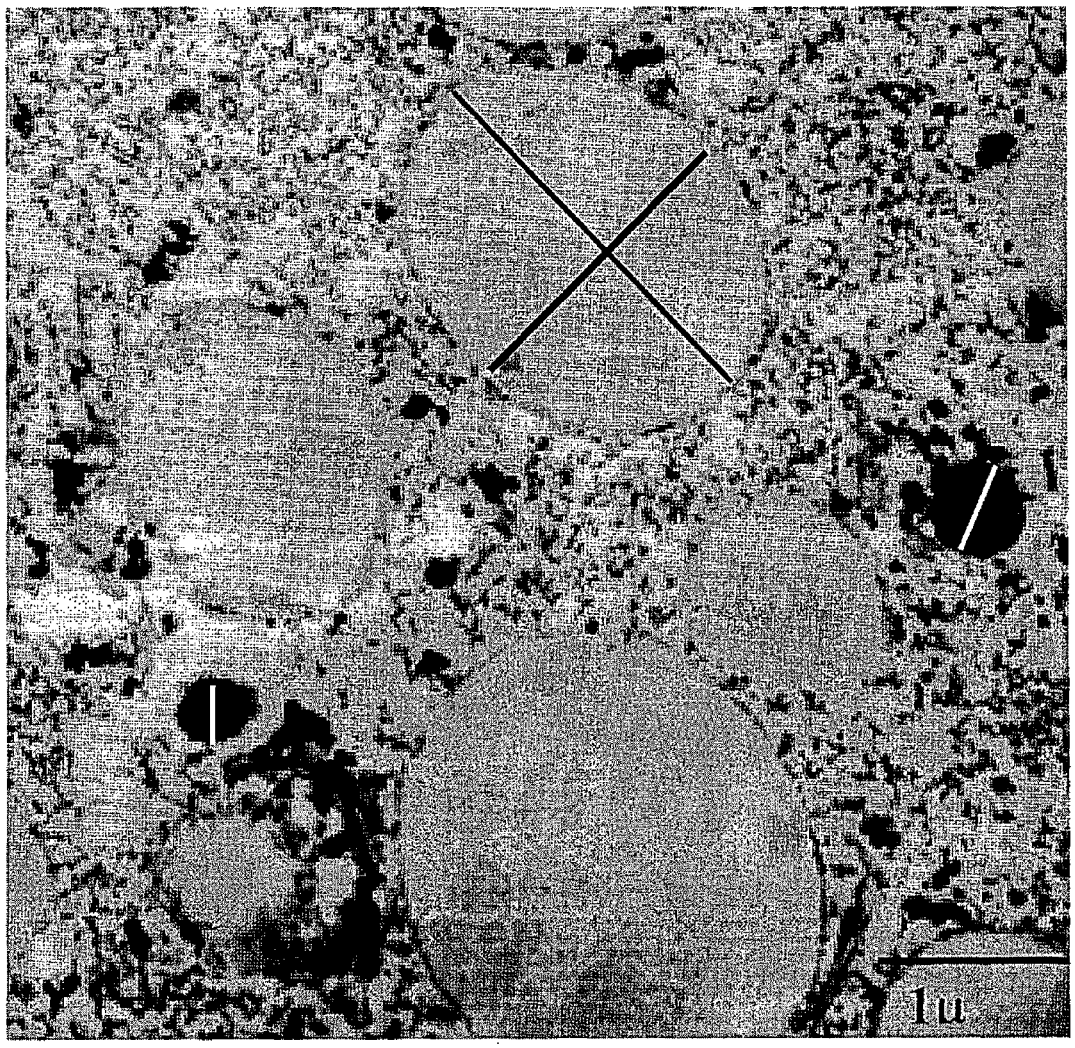
FIG. 5 shows dark medium sized electron-dense archaea of between 0.5-1.1 µm in diameter, and large clear, empty archaea of between 1.0-2.4 µm in diameter.
Figure 6:
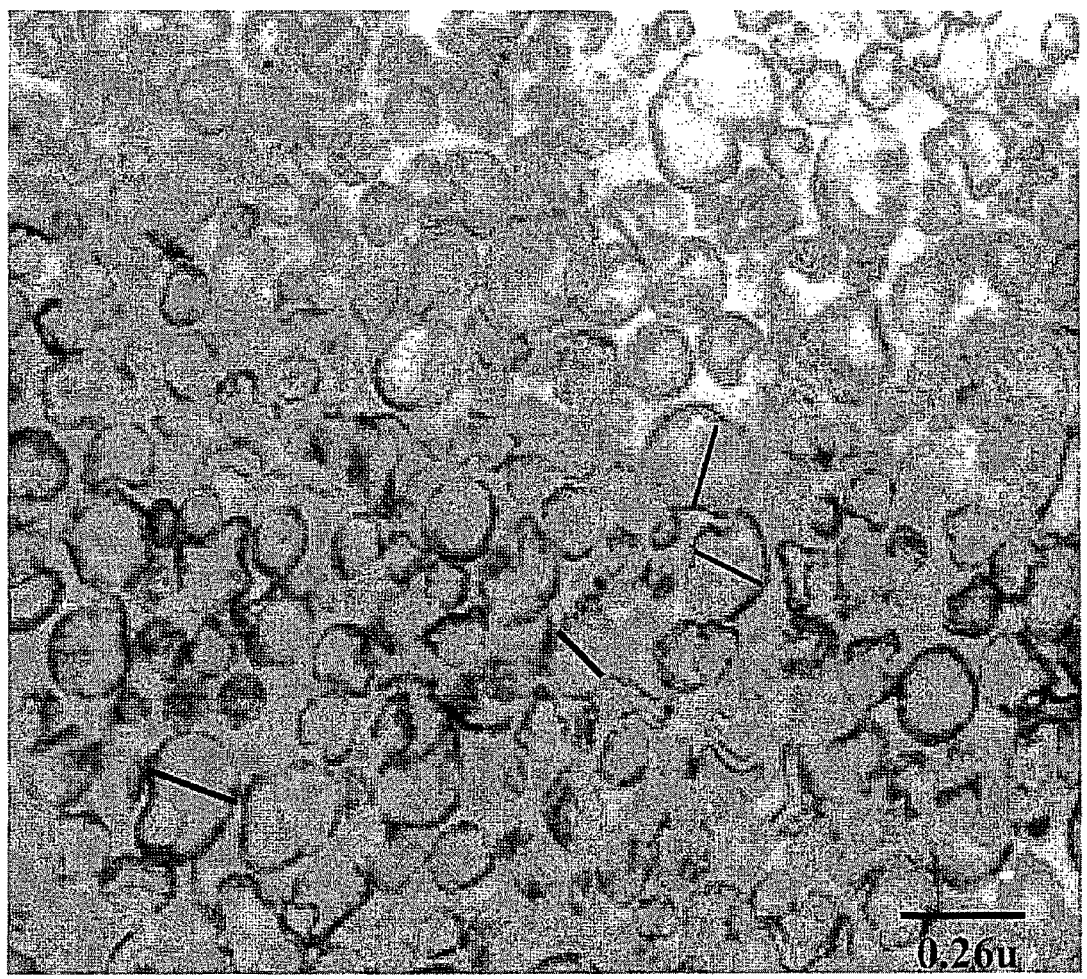
FIG. 6 shows clear, empty archaea of between 0.15-2.0 µm in diameter.

According to the invention, the purity of the plant extract may be determined by microscopic examination of the filtered, aged, plant extract, as described in U.S. Patent Application Publication No. 20050142116. For example, the filtered, aged plant extract can be stained with any DNA or RNA dye known in the art, such as acridine orange, bisbenzimide H 33342 (Hoechst), or 4',6-diamidino-2-phenylindole, dihydrochloride (DAPI); and viewed with an immunofluorescence optical microscope, an electron microscope, or any other microscope known in the art. Two forms of archaea, having different morphological characteristics may be identified. One type comprising an electron-dense content may be between about 0.03-0.15 μm (nanoparticle) and about 0.5-1.1 μm in diameter (medium particle) (FIGS. 4 and 5, respectively). A second type may comprises a clear, empty content, and may be about 0.15-2.4 μm in diameter (FIGS. 5 and 6). The clear, empty archaea are similar in morphology to the pathogenic archaea associated with lesions, while the electron dense archaea comprise the non-pathogenic archaea and nanoarchaea comprising DNA or RNA. Brilliant red particles, which may comprise metallic ions, may also adhere to the surface of the archaea. Optimum purity may be achieved when predominantly, preferably essentially, only fast moving electron-dense nanoparticles are visible. The presence of clear, empty archaea or large brilliant red particles of about 0.15-0.24 μm and at a concentration of, for example, ≥1.0 large brilliant red particle/visual field, indicates suboptimal purity. In cases of suboptimal purity, the filtered aged plant extract is subjected to additional filtration, for example, tangential flow filtration in the Minitan Ultrafiltration System (Millipore, Bedford, Mass., USA), using the microporous membrane packet (30,000 NMWL). In preferred embodiments, the compositions of the invention comprise a greater number of electron dense archaea (nanoparticles and medium particles) than empty, clear archaea; and a greater number of archaea not associated with large brilliant red particles than those associated with large brilliant red particles.

According to the invention, the purified plant extract may comprise an enriched population of particles. The concentration of particles may be between $1\times10^5$ and $1\times10^{10}$ particles/ml, more preferably between $1\times10^6$ and $1\times10^9$ particles/ml, and most preferably about $1\times10^7$ particles/ml.

In a non-limiting embodiment, the compositions of the invention comprise combinations of trans-sialidase, a metal chelator, and one or more purified plant extracts as shown in Table I.

TABLE I

Combinations of trans-sialidase, a metal chelator, and one or more purified plant extracts encompassed by the invention. Combinations of trans-sialidase (TS), pyrrolidine dithiocarbamate (PDTC), and purified plant extracts TS
TS + PDTC
TS + PDTC + *Allium sativum* (AS)
TS + PDTC + *Ginko biloba* (GB)
TS + PDTC + *Zingiber officinale* (ZO)
TS + PDTC + orchid extract (OE)
TS + PDTC + AS + GB
TS + PDTC + AS + ZO
TS + PDTC + AS + OE
TS + PDTC + AS + GB + ZO
TS + PDTC + AS + GB + OE
TS + PDTC + AS + GB + ZO + OE
TS + PDTC + AS + ZO + OE
TS + PDTC + GB + ZO
TS + PDTC + GB + OE
TS + PDTC + GB + ZO + OE
TS + PDTC + ZO + OE
TS + AS
TS + GB
TS + ZO
TS + OE
TS + AS + GB TABLE I-continued Combinations of trans-sialidase, a metal chelator, and one or more purified plant extracts encompassed by the invention. Combinations of trans-sialidase (TS), pyrrolidine dithiocarbamate (PDTC), and purified plant extracts TS + AS + ZO
TS + AS + OE
TS + AS + GB + ZO
TS + AS + GB + OE
TS + AS + GB + ZO + OE
TS + AS + ZO + OE
TS + GB + ZO
TS + GB + OE
TS + GB + ZO + OE
TS + ZO + OE

5.2 Therapeutic Uses

The present invention provides for compositions and methods for reducing the presence of atherosclerotic plaques in a blood vessel. In a preferred embodiment, the composition of the invention comprises a trans-sialidase enzyme, PDTC, and one or more purified plant extracts The compositions and methods of the invention further provide for reducing the level of total serum cholesterol in a treated subject, as well as serum LDL, HDL and triglyceride levels.

In one embodiment, the composition of the invention may be administered in an amount effective to reduce the presence of an atherosclerotic plaque. In a non-limiting embodiment of the invention, the composition may be administered systemically, for example, as an injection. In another preferred embodiment of the invention, the composition may be administered orally. According to the invention, the composition is effective to promote a reduction in the presence of one or more mycoplasma and one or more non-mycoplasma microorganism on a blood vessel wall as compared to a subject not treated with the composition. For example, the presence of *Mycoplasma pneumoniae* and *Chlamydia pneumoniae* is reduced in atherosclerotic plaques.

In another series of non-limiting embodiments, the composition may be administered as a single dose, or at regular intervals so that the composition is effective to promote a reduction in the presence or level of atherosclerotic plaques, total serum cholesterol, serum LDL, serum HDL, and triglyceride in a subject as compared to a subject not treated with the composition.

In a non-limiting embodiment of the invention, the composition may be administered in an amount effective to reduce the surface area of a blood vessel covered by an atherosclerotic plaque. The composition may decrease the percentage of a blood vessel's surface area occupied by a plaque to between about 0% and 75%, more preferable between 2% and 50%, more preferably between 5% and 60%, more preferably between 10% and 25% and most preferably about 11% of the total surface area of the blood vessel.

In another non-limiting embodiment of the invention, the composition may be administered in an amount effective to reduce the level of total serum cholesterol in a subject in need of treatment. The composition may reduce the level of total serum cholesterol of the subject by about 5%, 10%, 20%, 50%, 90% or 95% such that the level of total cholesterol is reduced to about the normal level found in a subject not in need of treatment.

In another non-limiting embodiment of the invention, the composition may be administered in an amount effective to reduce the level of serum LDL cholesterol in a subject in need of treatment. The composition may reduce the level of serum LDL cholesterol of the subject by about 5%, 10%, 20%, 50%, 90% or 95% such that the level of serum LDL cholesterol is reduced to about the normal level found in a subject not in need of treatment.

In another non-limiting embodiment of the invention, the composition may be administered in an amount effective to reduce the level of serum HDL cholesterol in a subject in need of treatment. The composition may reduce the level of serum HDL cholesterol of the subject by about 5%, 10%, 20%, 50%, 90% or 95% such that the level of serum HDL cholesterol is reduced to about the normal level found in a subject not in need of treatment.

In another non-limiting embodiment of the invention, the composition may be administered in an amount effective to reduce the level of triglycerides in a subject in need of treatment. The composition may reduce the level of triglycerides of the subject by about 5%, 10%, 20%, 50%, 90% or 95% such that the level of triglycerides is reduced to about the normal level found in a subject not in need of treatment.

In a further non-limiting embodiment of the invention, the normal level of total serum cholesterol is about 200 mg/dl or less, the normal level of serum LDL cholesterol is about 100 mg/dl or less, the normal level of serum HDL cholesterol is about 60 mg/dl or more, and the normal level of triglycerides is about 150 mg/dl or less (American Heart Association website, Jan. 30, 2007).

In another non-limiting embodiment of the invention, the composition may be administered in an amount effective to reduce the presence of one or more microorganism with an atherosclerotic plaque, for example, but not limited to *Mycoplasma pneumoniae* and *Chlamydia pneumoniae*, wherein the reduction in microorganism presence is indicated by a reduction in the detection of the microorganisms' antigens. According to the invention, the reduction in antigen detection is between about 0.1 and 100%, and most preferably 99% as compared to the antigen detection in an untreated subject.

The composition may be administered locally or systemically, for example, by injection, orally, occularly, rectally, topically, or by any other means known in the art. The composition may be ingested as a liquid, a pill, or a capsule (e.g. liquid or powder-filled).

In one non-limiting embodiment, the composition may comprise a trans-sialidase, a metal chelator, for example, but not limited to, PDTC, NTA, diphenylthiocarbazone(dithizone), histidine, DP-109, EGTA, EDTA, DMPS, Lysinoalanine, Synthetic lysinoalanine, tetracycline, ALA, Dimercaptosuccinic acid, DMSA, Calcium disodium versante, D-penicillamine, Deferoxamine, Defarasirox, Dimercaprol, and DTPA; and one or more purified plant extract. The trans-sialidase may have an enzymatic activity of between about 0.01 and 10 U/ml, more preferably between about 0.2 and 5 U/ml, more preferably between about 0.5 and 2 U/ml and most preferably about 1.0 U/ml. The metal chelator may have a concentration of between about 0.01 and 10 mg/ml, more preferably between about 0.5 and 5 mg/ml, more preferably between about 1 and 2 mg/ml, and most preferably 1.5 mg/ml. The purified plant extract may comprise a particle concentration of between about $1 \times 10^5$ and $1 \times 10^7$ particles/ml, more preferably between about $5 \times 10^6$ and $9 \times 10^6$ particles/ml, more preferably between about $2 \times 10^6$ and $3 \times 10^6$ particles/ml, and most preferably about $1.0 \times 10^6$ particles/ml.

In a specific non-limiting embodiment, the composition is administered as an injection, wherein the composition comprises a trans-sialidase, PDTC and one or more purified plant extract, further wherein the trans-sialidase has an enzymatic activity of 1.04 U/ml, the PDTC has a concentration of 1.5 mg/ml, and the purified plant extract has a particle concentration of $1.0 \times 10^6$ particles/ml.

In an alternative non-limiting embodiment, the composition may comprise a trans-sialidase, a metal chelator, and one or more purified plant extract, wherein the trans-sialidase comprises an enzymatic activity of between about $1 \times 10^{-8}$ and $1 \times 10^{-4}$ U/ml, more preferably between about $1 \times 10^{-7}$ and $1 \times 10^{-5}$ U/ml, more preferably between about $1 \times 10^{-6}$ and $5 \times 10^{-6}$ U/ml and most preferably about $1.5 \times 10^{-6}$ U/ml. The metal chelator may have a concentration of between about 0.01 and 10 mg/ml, more preferably between about 0.5 and 5 mg/ml, more preferably between about 1 and 2 mg/ml, and most preferably 1.5 mg/ml. The purified plant extract may comprise a particle concentration of between about $1 \times 10^5$ and $1 \times 10^7$ particles/ml, more preferably between about $2 \times 10^6$ and $9 \times 10^6$ particles/ml, more preferably between about $3 \times 10^6$ and $7 \times 10^6$ particles/ml, and most preferably about $5 \times 10^6$ particles/ml.

In a specific non-limiting embodiment, the composition is administered orally as a liquid, wherein the composition comprises a trans-sialidase and one or more purified plant extract, further wherein the trans-sialidase has an enzymatic activity of $1.3 \times 10^{-6}$ U/ml and the purified plant extract has a particle concentration of $5.0 \times 10^6$ particles/ml.

In another non-limiting embodiment, the composition is administered in an amount of between 0.002 and 5.0 ml/kg, more preferably between 0.1 and 2.0 ml/kg, more preferably between 0.2 and 1.0 ml/kg, and most preferably about 0.25-0.5 ml/kg.

In a further non-limiting embodiment, the composition may be administered once, twice, three, four, five, or six or more times per day during the treatment period. Alternatively, the composition may be administered once every two, three, four, five, six or seven or more days.

In a non-limiting example of the invention, the composition is a mixture of trans-sialidase and PDTC, wherein the trans-sialidase has an activity of about 1.04 U/ml and the PDTC is at a concentration of 1.5 mg/ml, and wherein the composition is administered via intraperitoneal or intravenous injection at a volume of .about 25-0.5 ml/kg every other day.

In a further non-limiting example of the invention, the mixture of trans-sialidase and PDTC is supplemented with a purified plant extract diluted 1:10 in purified water, and containing an average of $1.0 \times 10^6$ nanoparticles/ml. The plant extract dilution is administered through intraperitoneal injections once per day for a four week treatment period. Examples of mixtures include, but are not limited to, TS+PDTC, TS+PDTC+AS extract, TS+PDTC+AS+GB extracts, and TS+PDTC+AS+GB+ZO extracts. For each of the mixtures, the TS+PDTC may be injected intravenously or ingested orally in an amount of 0.25-0.5 ml/kg every other day during a 12 week treatment session, wherein the mixture comprises 1.04 U/ml TS activity and 1.5 mg/ml PDTC. Each of the plant extracts comprise a 1:10 plant extract:water dilution which further comprise $1.0 \times 10^6$ nanoparticles/ml. A total volume of 1 ml of diluted plant extract is injected intraperitoneally once daily during the 12 week treatment period. When more than one diluted plant extract is used, the different extracts are mixed in equal volumes.

The present invention also provides for methods of diagnosing, preventing and treating a disorder characterized by undesirable cell proliferation, for example, atherosclerosis and mycoplasma associated diseases. In one embodiment of the invention, diagnosis of atherosclerosis and/or a mycoplasma associated disease is performed by detecting the presence of an agent in the serum, blood or plasma of a patient, wherein detection of the agent indicates the existence or likelihood of developing atherosclerosis and/or a mycoplasma associated disease. In other embodiments of the invention, diagnosis is performed by detecting the presence of the agent in an atherosclerotic lesion. The presence of the agent may be detected, for example, using electron microscopy, fluorescence microscopy, immunohistochemistry, or any other method known in the art.

In one non-limiting embodiment, the agent is mycoplasma or a mycoplasma lipoprotein, for example, *Mycoplasma pneumoniae* lipoprotein.

In other non-limiting embodiments, the agent is chlamydia or a chlamydia lipopolysaccharide (LPS), for example, *Chlamydia pneumoniae* LPS.

In other non-limiting embodiments, the agent is a pathogenic archaea.

In other non-limiting embodiments, the agent is C reactive protein (CRP).

In other non-limiting embodiments, the agent is spirochete.

In one non-limiting embodiment of the present invention, detecting the presence of mycoplasma, mycoplasma lipoprotein, CRP, or a combination thereof, in serum of a patient indicates a diagnosis of atherosclerosis, coronary artery disease (CAD), or the presence of a stable atheroma in the patient.

In other non-limiting embodiments of the present invention, detecting the presence of chlamydia, chlamydia LPS, pathogenic archaea, or a combination thereof, in serum of a patient indicates a diagnosis of acute myocardial infarction (AMI), or the presence of an unstable or ruptured atheroma in the patient.

In one non-limiting embodiment of the invention, the agent can be concentrated from the serum and plasma of a subject (e.g., a human patient) before detecting the presence of the agent. For example, serum can be separated from blood by incubating a blood sample in a water bath to form a blood clot. The serum can be isolated from the blood clot by centrifuging the sample to obtain a supernatant comprising the serum. The serum can then be prepared for electron microscopy analysis by fixing the serum (e.g., by combining 1 ml of serum with 1.0 ml of glutaraldehyde fixative and 1.0 ml of Osmium tetroxide), centrifuging the treated serum, and sectioning the resulting pellet. The supernatant can also be analyzed using electron microscopy for agent detection.

In other non-limiting embodiments of the invention, success of treatment for atherosclerosis and/or a mycoplasma associated disease can be determined by detecting archaea and/or mycoplasma and/or chlamydia and/or spirochete forms or their products in the serum or atherosclerotic lesions of a patient. In one non-limiting embodiment, a decrease in the number of archaea and/or mycoplasma and/or chlamydia and/or spirochete forms or their products in the serum or in the atherosclerotic lesions of a patient indicates successful treatment.

In one non-limiting embodiment, a method for monitoring success of treatment for a disorder characterized by undesirable cell proliferation in a subject comprises obtaining a first sample from the subject; obtaining a second sample from the subject, wherein the second sample is obtained after the first sample; and detecting the presence of an agent (e.g., archaea and/or mycoplasma and/or chlamydia and/or spirochete) in the first and second samples, wherein a decrease in the number or concentration of agent in the second sample compared to the first sample indicates treatment success.

6 EXAMPLES

Example 1

Treatment of Aortic Atherosclerotic Plaques in Rabbits with Trans-Sialidase, PDTC, and Plant Extracts The present study compares the effects of trans-sialidase (TS) enzyme derived from *Trypanosoma cruzi*, PDTC and one or more aged plant extracts derived from *Allium sativum* (AS), *Ginkgo biloba* (GB) and *Zingiber officinale* (ZO), on the reduction of aortic atherosclerotic plaques, lipid serum levels and infectious agent antigens at intima in rabbits receiving cholesterol-rich-diet.

Material and Methods

White New Zealand male rabbits of approximately 2 months in age, weighing 2.2±0.5 kg were included in the study. The study lasted 12 weeks. The rabbits were divided into six different treatment groups. Group I animals received normal rabbit chow, while Groups II-VI received normal rabbit chow supplemented with 1% cholesterol. Animals received the diets for a period of 12 weeks. Groups III-VI also received anti-atherosclerotic treatment during the final 4 weeks of the study. The feeding and treatment schedule is shown in Table II.

TABLE II

Feeding and treatment schedule for the six study Groups.

| Group | Number of Rabbits in Group | Diet | Anti-Atherosclerotic Treatment (final 4 weeks of study) |
|---|---|---|---|
| GI. | 13 | Normal rabbit chow | None |
| GII. | 13 | Normal rabbit chow + 1% cholesterol | None |
| GIII. | 5 | Normal rabbit chow + 1% cholesterol | TS + PDTC |
| GIV. | 5 | Normal rabbit chow + 1% cholesterol | TS + PDTC + AS extract |
| GV. | 5 | Normal rabbit chow + 1% cholesterol | TS + PDTC + AS + GB extracts |
| GVI. | 5 | Normal rabbit chow + 1% cholesterol | TS + PDTC + AS + GB + ZO extracts |

Diet Preparation

Nuvilab® (Nuvital. Curitiba, PR. Brazil) was used as the normal rabbit chow in the study. Normal rabbit chow supplemented with 1% cholesterol was prepared by adding 10 g of cholesterol powder (Sigma-C 8503) dissolved in a solution of 50 ml ethylic ether and 100 ml 70% ethanol, to each Kg of normal rabbit chow Trans-Sialidase (TS) Preparation

*Trypanosoma cruzi* were cultured according to Kloetzel et al. (Kloetzel et al., 1984, *Trypanosoma cruzi* interaction with macrophages: differences between tissue culture and bloodstream forms. Rev. Inst. Med. Trop. Sao Paulo, 26:179-85). Supernatant from the culture was filtered through a 1 µm pore filter in a vacuum chamber, or the supernatant was filtered through a 0.22 µm filter and concentrated by precipitation with 50% $(NH_4)_2SO_4$. The precipitates were dialyzed against phosphate-buffered saline, and then passed through a tresyl-agarose column containing an immobilized anti-trans-sialidase monoclonal antibody. The column was washed with phosphate-buffered saline, followed by a 10 mM sodium phosphate, pH 6.5 wash. The trans-sialidase was eluted with a 3.5 mM $MgCl_2$, 10 mM sodium phosphate, pH 6.0 solution. The fractions eluted from the column were immediately filtered through a Sephadex G-25 column equilibrated with 20 mM Tris-HCl, pH 8.0, to remove $MgCl_2$. The trans-sialidase was further purified by passage through a Mono Q column equilibrated in 20 mM Tris-HCl, pH 8.0, and eluted with a linear gradient from 0 to 1 m NaCl in the same buffer.

The purified enzyme derived from the culture comprises a 400 kDa multimeric aggregate. The enzymatic activity of the purified trans-sialidase was measured according to methods described in International Patent Application No. PCT/BR01/00083, filed Jul. 3, 2001. Purified trans-sialidase used in the study had an enzymatic activity of 1.3 U/ml.

Plant Extract Preparation

Plant (*Allium sativum* (AS) cloves, *Ginkgo biloba* leaves (GB) and *Zingiber officinale* (ZO) raw) extracts were prepared by introducing sliced plant tissue into a 10-20% aqueous ethanol solution. The plant/ethanol mixture was adjusted to a final proportion of 40:60 plant weight:ethanol and stored for up to 12 months at room temperature in a dark, anaerobic environment (in a sealed bottle). Following storage, the plant mass/alcohol mixture was passed through Whatman qualitative filter paper grade 1, diameter 24 cm, pore size 11 µm. The liquid filtrate was then filtered again in a vacuum chamber with a 47 mm diameter glass microfiber filter, pore size 1.1 µm. Then filtrate was next filtered through successively smaller pores, in a tangential flow device (Minitan Ultrafiltration Millipore System-Millipore, Bedford, Mass., USA), using the microporous membrane packet (30,000 NMWL) that concentrates large particles. The filtrated portion of the extract was used in the study.

Trans-Sialidase (TS)+PDTC Anti-Atherosclerotic Treatment

Rabbits were treated with 0.25-0.5 ml/kg of a trans-sialidase+PDTC mixture injected intraperitoneally on alternative days. 1 ml of the treatment mixture comprised 0.8 ml of *Trypanosoma cruzi* culture supernatant (enzymatic activity of 1.3 U/ml) and 1.5 mg of PDTC (pyrrolidine dithiocarbamate ammonium salt from ICN Biomedicals Inc., Aurora, Ohio, USA.) dissolved in 0.2 ml of saline.

Trans-Sialidase (TS)+PDTC+Plant Extract Anti-Atherosclerotic Treatment

Animals were treated with the trans-sialidase+PDTC solution as described above along with 1 ml of a purified plant extract dilution containing an average of $1 \times 10^6$ nanoparticles. The plant extract dilution was administered through intraperitoneal injections once per day during the four week treatment period. The purified plant extract dilution was generated by diluting an aged ethanolic plant extract 1:10 in water.

Serum Lipid Analysis

Serum lipid analysis was performed at the beginning and end of the 12 week experiment. To obtain the blood serum, a 10 ml blood sample was taken from each animal through cardiac puncture, and centrifuged at 1500 g for 15 min at 4° C. Total cholesterol, high-density lipoprotein (HDL) and triglycerides concentrations were determined by enzymatic methods (CHOD-PAP Merck®, USA. and GPO-PAP Cobas Mira, Roche).

Aortic Atherosclerotic Lesions Analysis

To analyze aortic atherosclerotic lesions, rabbits were euthanized with an intramuscular injection of 25 mg/kg Ketamine and 2-5 mg/kg Xilazina. Aorta were excised and opened longitudinally along the anterior wall, washed in saline, stretched on cardboard, and placed in 10% buffered formalin. Aorta were then stained with Sudan IV. Intimal positive areas stained in red by Sudan IV were measured by automatic detection using an image analysis system (Quantimet 500, Leica).

Histological examination of the aorta were also performed. A 1 cm thickness cross-section of the initial descending thoracic aorta were taken and embedded in paraffin. 5 μm serial sections of the cross-section were submitted to H&E stain and immunohistochemical detection of *Mycoplasma pneumoniae* (MP) and *Chlamydia pneumoniae* (CP) antigens, as previously described. (Fagundes R Q. Study of co-participation of natural infection by *Chlamydophila pneumoniae* and *Mycoplasma pneumoniae* in experimental atherogenesis in rabbits. Doctoral thesis presented at the Heart Institute of Clinical Hospital, in the Cardiology Sciences Post graduation Program of Sao Paulo University School of Medicine, Mar. 17, 2006). The percentage of area positive for infectious agent antigens on the immunostained slides was determined using an automatic color detection system (Image Analysis System Quantimet 500, Leica, Germany).

Results

The mean and standard deviation values of percentage areas of fat plaques (macroscopically) and of MP and CP antigens at intima, and intimal area in 1 cm cross section are shown at table III. Lipid levels in the serum are reported at table IV.

Atherosclerotic Plaques and Lipid Levels

The control group, Group I, which received normal rabbit chow and no ant-atherosclerotic treatment, did not develop plaques on the aortal walls. Trace amounts of MP and CP antigens on the aorta wall were detected, but in all cases, without development of atheroma plaques.

Figure 1:
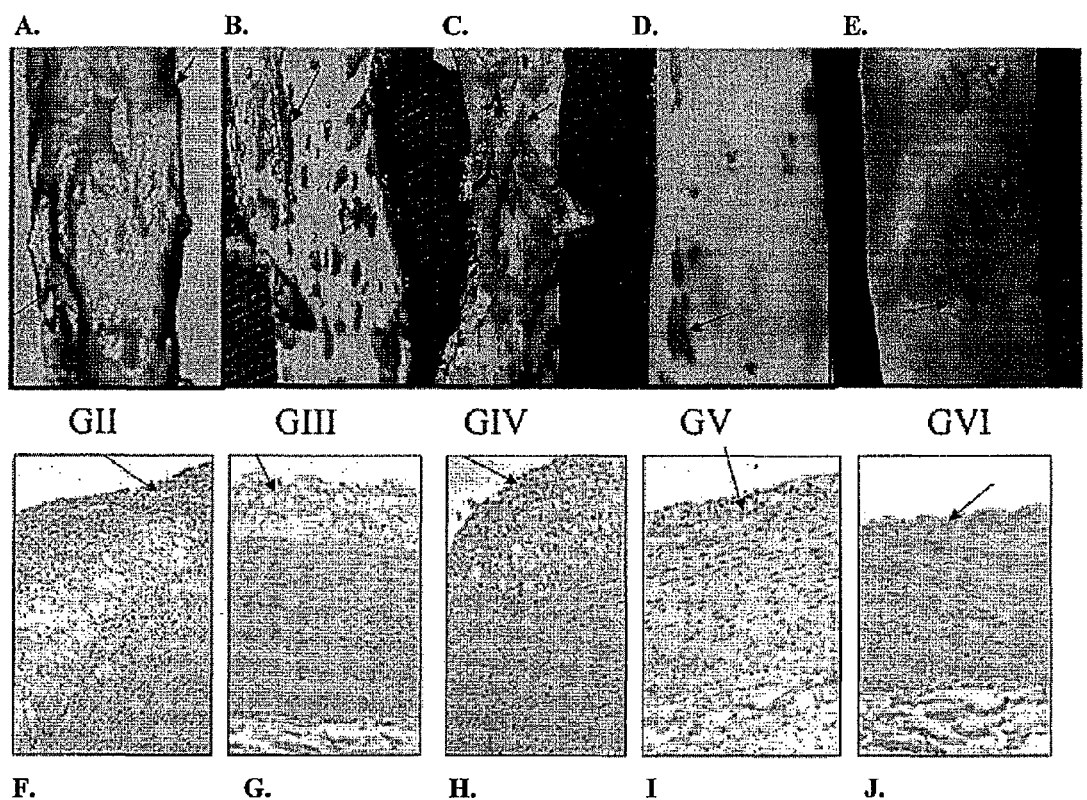

Group II, which received normal food supplemented with 1% cholesterol and no anti-atherosclerotic treatment, presented 75% coverage of the aorta intimal surface by severe lipid atheroma plaques stained with Sudan IV. (FIG. 1). The histology revealed that the plaques were comprised of 89% fat.

Group III, which received normal food supplemented with 1% cholesterol and treatment with TS+PDTC, exhibited 50% coverage of the aorta intimal surface by severe lipid atheroma plaques stained with Sudan IV. (FIG. 1).

Groups IV, V and VI, which received normal food supplemented with 1% cholesterol and treatment with TS+PDTC+ Plant extracts, presented progressively smaller areas of atherosclerotic plaque coverage of the aorta wall (Table III). The addition of AS to the treatment regime reduced the levels of total cholesterol and HDL in the blood serum (Table IV), but did not reduce the % plaque area of atheroma (Table III), and induced a decrease in aorta perimeter, indicating a negative remodeling of the vessel. The addition of AS+GB to the treatment led to a significant reduction in both % area of intimal plaques and cholesterol levels in the serum. The most effective anti-atherosclerotic effect was observed with a complex of plant extracts from AS, GB and ZO, which reduced the area of the aorta wall covered by plaque to 11%, and returned lipid levels in the serum to normal levels (Table IV). Most of the remaining intimal plaques were fibrotic, largely free of foam cells (FIG. 1). Treatment with AS, GB and ZO extracts reduced both intimal area and % of intraplaque fat (Table III).

TABLE III

Intimal Area and Percentage Areas of Aorta Atheroma Plaques, Fat and Infectious Agents in Aortic Plaques of 1% Cholesterol-Fed Rabbits Submitted to Different Treatments.

| Group | % area C. pneumoniae+ Mean (SD) | % area M. pneumoniae+ Mean (SD) | % Plaque area - macroscopic Mean (SD) | % plaque fat Mean (SD) | Intima area ($mm^2$) Mean (SD) |
|---|---|---|---|---|---|
| GI   | 0.007 (0.005) | 0.013 (0.012) | 0.0 (0.0) | 0.0 (0.0) | 0.0 (0.0) |
| GII  | 23.50 (5.66)  | 25.60 (3.96)  | 75 (9)    | 89 (5)    | 75 (7)    |
| GIII | 16.04 (0.60)  | 12.81 (1.27)  | 50 (3)    | 50 (3)    | 65 (4)    |
| GIV  | 12.60 (0.85)  | 10.53 (0.51)  | 67 (14)   | 61 (10)   | 61 (8)    |
| GV   | 8.60 (0.21)   | 4.57 (0.51)   | 42 (8)    | 40 (14)   | 39 (6)    |
| GVI  | 0.022 (0.005) | 0.02 (0.005)  | 11 (1)    | 17 (10)   | 17 (2)    |

TABLE IV

Cholesterol Fractions and Triglycerides Serum Levels of 1% Cholesterol-Fed Rabbits Submitted to Different Treatments. Values shown are in mg/dl.

| Group | Total cholesterol Mean (SD) | p | Triglycerides Mean (SD) | p | HDL Mean (SD) | p | LDL Mean (SD) | p |
|---|---|---|---|---|---|---|---|---|
| GI   | 67 (31)    | 0.17   | 64 (13)  | 0.01   | 42 (7)   | <0.01  | 33 (24)  | 0.09   |
| GII  | 1029 (237) | <0.01  | 115 (55) | <0.01  | 210 (52) | <0.01  | 775 (227)| <0.01  |
| GIII | 873 (82)   | 0.09   | 95 (10)  | 0.22   | 175 (17) | 0.08   | 743 (92) | 0.38   |
| GIV  | 778 (58)   | 0.02   | 86 (9)   | 0.13   | 115 (11) | <0.01  | 635 (60) | 0.10   |
| GV   | 408 (69)   | <0.01  | 51 (6)   | <0.01  | 90 (6)   | <0.01  | 335 (29) | <0.01  |
| GVI  | 53 (6)     | <0.01  | 47 (8)   | 0.26   | 36 (3)   | <0.01  | 18 (6)   | <0.01  |

GI—control group not receiving cholesterol diet; GII—non treated; GIII—received trans-sialidase (TS) and pyrrolidine dithiocarbamate (PDTC); GIV—received TS + PDTC + *Allium Sativum* extract (AS); GV—treated with TS + PDTC + AS + *Ginkgo biloba* extract (GB) and GVI—received TS + PDTC + AS + GB + *Zingiber officinale* extract; SD—standard deviation
p—represents difference regarding the respective values of the above group, except GI values which were compared with group GVI (level of significance 5%)

*Mycoplasma pneumoniae* and *Chlamydia pneumoniae* Antigens

Treatment with TS+PDTC (Group III) reduced the percent area of MP antigen expression from 25.6±3.96 to 12.81±1.27 (p<0.01) and CP antigen expression from 23.50±5.66 to 16.04±0.60 (p<0.001) as compared to Group II animals that received no anti-atherosclerotic treatment. Addition of plant extracts caused a progressively more significant decrease in percentage area positive for CP and MP antigens at intima. When all three plant extracts were used in the anti-atherosclerotic treatment, the reduction was more effective. Use of all three extracts reduced the percentage of total area expressing MP antigen to 0.02±0.005 and CP antigens to 0.022±0.005. These values were similar to the control group (Group I) (Table III). Macroscopic and microscopic aspects of different groups are exemplified at the FIG. 1.

Conclusion

In conclusion, the present study indicates a new formulation for the treatment of atherosclerosis, using a combination of *T. cruzi* trans-sialidase, PDTC and three aged plant extracts: *Allium sativum, Ginkgo biloba* and *Zingiber officinale*. Treatment with these compounds was effective in reducing intimal accumulation of both fat and *C. pneumoniae* plus *M. pneumoniae* antigens. The lipid serum levels returned to normal levels even in the permanence of a cholesterol rich diet.

Example 2

Treatment of Human Patients Exhibiting High Total Cholesterol and LDL Levels with Trans-Sialidase and Plant Extracts Three volunteers who presented high levels of total cholesterol and LDL cholesterol fraction in blood serum were treated with purified trans-sialidase and aged plant extracts.

Materials and Methods

Plant Extract Preparation

Plant (*Allium sativum* (AS) cloves, *Ginkgo biloba* leaves (GB). *Zingiber officinale* raws (ZO) and *Pfaffia paniculata* (Brazilian ginseng) roofs (GS)) extracts were prepared by introducing sliced plant tissue into a 10-20% aqueous ethanol solution. The plant/ethanol mixture was adjusted to a final proportion of 40:60 plant weight:ethanol and stored for up to 12 months at room temperature in a dark, anaerobic environment (in a sealed bottle). Following storage, the plant mass/alcohol mixture was passed through Whatman qualitative filter paper grade 1, diameter 24 cm, pore size 11 μm. The liquid filtrate was then filtered again in a vacuum chamber with a 47 mm diameter glass microfiber filter, pore size 1.1 μm. Then filtrate was next filtered through successively smaller pores, in a tangential flow device (Minitan Ultrafiltration Millipore System, Millipore, Bedford, Mass., USA), using the microporous membrane packet (30,000 NMWL) that concentrates large particles. The filtrated portion of the extract was used in the experiments.

Recombinant Trans-Sialidase Purification

Recombinant trans-sialidase was produced and purified from the *Escherichia coli* strain BLB21 DE3 inserted with a pTSII plasmidium comprising the *T. cruzi* trans-sialidase gene as described in International Patent Publication WO/2002/002050 by Higuchi et al., published Jan. 10, 2002.

The protein concentration of 5 mg/ml was produced as measured with a spectrophotometer. The recombinant trans-sialidase was diluted in a buffer liquid (TBS+BSA 0.2%), and the activity was measured according to previously described methods (International Patent Publication WO/2002/002050). The purified enzyme was diluted 1:10,000 and 1:100,000 resulting in enzymatic activities of 15,000 and 5,000 CPM, respectively. For human oral administration, the trans-sialidase was diluted 1:1,000,000 (0.005 mg/ml) in MilliQ purified water, and stored at 4° C.

Preparation and Administration of Oral Drug

Equal proportions of pure extracts from *Allium sativum* (AS); *Ginkgo biloba* (GB) *Zingiber officinale* (ZO) and ginseng (GS) were mixed. The mixture was then diluted 1:1 in thermal water (from Irai, RS, Brazil), which was previously boiled and filtered.

Trans-sialidase diluted 1:1,000,000 (0.005 mg/ml) was administered to the subjects. A mean of 200 ul to 500 ul (4-10 drops) of diluted trans-sialidase was added in a glass of water and ingested daily.

Three volunteers who presented high levels of total cholesterol and serum LDL cholesterol were treated with the oral compositions for a minimum of 30 days to over one year. The volunteers were administered orally 200 ul of the diluted plant extract composition 2×/day, and 200 ul of the diluted trans-sialidase composition 1×/day. The patients were also being treated with other anti-cholesterol drugs (statins). Following treatment, the volunteers presented normal total cholesterol and serum LDL cholesterol levels, wherein the mean level of decrease in serum cholesterol levels following treatment was 20%. This decrease was observed even if statins had been previously used to lower serum cholesterol levels.

Example 3

Tobacco Extracts Contain Large Lipidic Pathogenic Archaea that can be Removed by Incubation in Thermal Water Tobacco Extracts:

Tobacco extracts were obtained by removing the contents from a packet of commercial tobacco cigarettes, and adding the contents to 80 ml of water. The tobacco/water mixture was then mixed with 500 ml of ethanol (92% ethanol). The tobacco/water/alcohol mixture was then aged in a sealed bottle for 12 months. Following 12 moths of aging, the mixture was filtered through Whatman qualitative filter paper (grade 1, diameter 24 cm, pore size 11 μm). The filtrate was then filtered a second time through vacuum chambers comprising a 47 mm diameter glass microfiber filter with a pore size of 1.1 μm.

The filtrate was analyzed with fluorescent and electron microscopy as described in U.S. Patent Application Publication No. 20050142116. Fluorescent microscopy of filtrate stained with acridine orange showed a large number of both large particles and nanoparticles containing DNA or RNA, but the filtrate was predominated by the large particles.

Analysis of the filtrate with electron microscopy showed that the two particles were the two types of archaea described previously: very small and clear structures of about 0.03-0.15 μm in diameter (see FIG. 4), which correspond to non-pathogenic archaea; and large particles (0.15-0.24 μm), along with other electron dense lipidic structures, which correspond to pathogenic archaea (see FIG. 5). The large archaea particles may also be observed as round brilliant red particles under fluorescent microscopy.

The pathogenic large particle archaea are also found in human periadventitial adipose tissue of atherosclerotic aortic aneurysms Analysis of human periadventitial adipose tissue of atherosclerotic aortic aneurysms with electron microscopy showed that this tissue contained a large number of the large lipidic particles surrounded by inflammatory infiltrate archaea surrounded by inflammatory lymphocytes (FIG. 6) suggesting that the particles are recognized as foreign structures by the immune system. High magnification of theses lipidic particles (FIG. 7) shows that the particles contain a clear external membrane, indicating that these particles correspond to microbes (large lipidic archaea), and not to lipidic droplets in the cytoplasm. These lipidic large archaea have the same morphology as the large particles that predominate tobacco extract, and as shown in FIGS. 5 and 6.

Preparation of the Therapeutic Extract from Tobacco:

As described previously, diluting and aging plant ethanolic extracts results in an extract enriched with non-pathogenic archaes (see U.S. Patent Application Publication No. 20050142116). For example, diluting an ethanolic plant extract with thermal medicinal water (from Irai city in South of Brazil) in a proportion of 1:10 (extract/water), and aging the mixture for 30 days, results in a reduction of the large lipidic archaea particles, while retaining the small non-pathogenic archaea. Extracts with enriched non-pathogenic archaea have been shown to be useful in the treatment of atherosclerosis and lowering serum lipids. Accordingly, tobacco extract prepared as described above and aged for 12 months was diluted 1:10 in thermal water, and aged for an additional 30 days.

Atherosclerosis was induced in a rabbit by feeding the rabbit with a high cholesterol diet (5% cholesterol) for 12 weeks. Following the 8 weeks of the feeding period, 0.5 ml samples of the aged 1:10 tobacco extract/thermal water mixture (which was enriched with non-pathogenic archaea) was subcutaneously injected into the rabbit's ear, twice a week, during the last 4 weeks of cholesterol enriched diet program. The animal was then sacrificed followed by macroscopic and microscopic analysis of the ascending and descending thoracic aorta. Both analyses did not show any atheroma plaques in the ascending or descending thoracic aorta, which are normally present following a cholesterol enriched feeding program (see FIG. 1).

Conclusion

The use of thermal medicinal water to dilute aged ethanolic plant extracts is effective in eliminating undesirable pathogenic large particle archaea, and preserving non-pathogenic archaea present in the extracts. Such an observation is observable by direct visualization of the plant extract mixture with fluorescent microscopy before and after diluting the extract with thermal water. Thus, the use of thermal water to purify plant extracts may increase the therapeutic and medicinal properties of the extracts. For example, non-pathogenic archaea present in tobacco extract may be enriched through purification with thermal water, and used to treat cholesterol induced atherosclerosis. One hypothetical mechanism of the success of such a treatment is that in human atherosclerotic lesions, such as aneurysms or unstable plaques that cause myocardial infarction, there are higher numbers of pathogenic archaea. These pathogenic arachae in the lesions may be increased by the use of tobacco products. Surprisingly, increasing the non-pathogenic archaea present in tobacco extracts by diluting the extracts with thermal water, may enable tobacco to be used as a treatment to combat the pathogenic archaea and atherosclerosis.

Example 4

Evaluation of Serum Sample from Patient with Coronary Artery Disease (CAD)

Lipoprotein from *Mycoplasma pneumoniae* and lipopolysaccharide (LPS) from *Chlamydia pneumoniae* were detected in the serum, by immunoelectron microscopy.

One ml of serum from the patient was processed to detect lipid particles, such as archaea. Lipoprotein from *Mycoplasma pneumoniae* was in greater amount in the serum of atherosclerotic patients and LPS from *Chlamydia pneumoniae* was increased in the serum of patients with acute myocardial infarction. Particles of C reactive protein (CRP) were also detectable by immunoelectron microscopy and their number increased in correlation with the number of mycoplasmal lipoprotein. The mean numbers of CRP and *Mycoplasma pneumoniae* particles/$mm^2$ of electron microscopy photos were higher in CAD patients (1.45+/−0.50 and 1.32+/−1.35) than in healthy subjects with similar age (1.05+/−0.29 and 0.26+/−0.20) ($p<0.01$), and were correlated with each other only in atherosclerotic patients group. The success of treatment may therefore be determined by measuring the particles of lipoprotein from mycoplasma, LPS from *Chlamydia pneumoniae* or pathogenic archaea in the serum, as shown in FIG. 9.

Example 5

Detection of Archaea and Microbes in Serum

Archaea and other microbes were concentrated from human serum and plasma using a modified technique for separating mitochondria and other organelles from tissue (Bustamante et al., Biochemical and Biophysical Research Communications. 334:907-910, 2005).

To separate serum from blood, 10 ml of blood was incubated for 1 hour in a water bath to form a blood clot that could be separated from the supernatant. Serum was isolated from the supernatant and blood clot by centrifuging the mixture at 2000 rpm for 5 minutes.

1 ml of serum was then prepared for electron microscopy by adding 1.0 ml of glutaraldehyde fixative and 1.0 ml of Osmium tetroxide to the serum. The treated serum was then centrifuged, and the resulting pellet was processed and embedded in glutaraldehyde. Thin sections of the pellet were prepared and examined under an electron microscope.

H medium (200 mM D-mannitol, 70 mM sucrose, 2 mM Hepes and 0.5 g/L defatted BSA, pH 7.2) was added to the remaining serum and centrifuged at 11400 rpm for 12 minutes at 4° C. The resulting supernatant and pellet were collected. The pellet was resuspended in H medium, and both the pellet and supernatant were analyzed using electron microscopy and PCR.

Results

The supernatants of the serum were predominantly rich in clear double membrane surrounding vesicles containing archaeal DNA, while the pellets contained mainly electron dense structures suggestive of ricketsia, *Chlamydia*, spirochete, and mycoplasma bodies.

Various publications are cited herein, the contents of which are hereby incorporated by reference in their entireties.

What is claimed is:

1. A method for monitoring success of treatment for a disorder characterized by undesirable cell proliferation selected from the group consisting of atherosclerosis, acute myocardial infarction, and coronary artery disease in a subject comprising:
    (a) obtaining a first sample from the subject;
    (b) obtaining a second sample from the subject, wherein the second sample is obtained after the first sample, and after administration of the treatment for the disorder;
    (c) detecting the presence of an agent in the first and second samples, wherein the agent is selected from the group consisting of pathogenic archaea, pathogenic archaea nucleic acid, mycoplasma, chlamydia, C reactive protein, spirochete, electron dense lipidic particle associated with archaea nucleic acid, electron lucent lipidic particle associated with archaea nucleic acid, and combinations thereof, and wherein a decrease in the number or concentration of the agent in the second sample compared to the first sample indicates treatment success.

2. The method of claim 1, wherein the first and second samples are each selected from the group consisting of serum, blood, plasma and atherosclerotic lesion.

3. The method of claim 1, wherein the agent is selected from the group consisting of mycoplasma, C reactive protein, electron dense lipidic particle associated with archaea nucleic acid, electron lucent lipidic particle associated with archaea nucleic acid, and combinations thereof.

4. The method of claim 1, wherein the agent is electron lucent lipidic particle associated with archaea nucleic acid.

* * * * *

SEQUENCE LISTING

<160> NUMBER OF SEQ ID NOS: 4

<210> SEQ ID NO 1
<211> LENGTH: 28

```
<212> TYPE: DNA
<213> ORGANISM: Artificial Sequence
<220> FEATURE:
<223> OTHER INFORMATION: Synthetic oligonucleotide

<400> SEQUENCE: 1
ggaattccat atggcacccg gatcgagc                                      28

<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 2
cggatccggg cgtacttctt tcactggtgc cggt                               34

<210> SEQ ID NO 3
<211> LENGTH: 2010
<212> TYPE: DNA
<213> ORGANISM: Artificial Sequence
<220> FEATURE:
<223> OTHER INFORMATION: Variant of T. Cruzi trans-sialidase gene.

<400> SEQUENCE: 3
atgggcagca gccatcatca tcatcatcac agcagcggcc tggtgccgcg cggcagccat     60
atggcacccg gatcgagccg agttgagctg tttaagcggc aaagctcgaa ggtgccattt    120
gaaaagggcg gcaaagtcac cgagcgggtt gtccactcgt tccgcctccc cgcccttgtt    180
aatgtggacg gggtgatggt tgccatcgcg gacgctcgct acgaaacatc caatgacaac    240
tccctcattg atacggtggc gaagtacagc gtggacgatg gggagacgtg ggagacccaa    300
attgccatca agaacagtcg tgcatcgtct gtttctcgtg tggtggatcc cacagtgatt    360
gtgaagggca acaagcttta cgtcctggtt ggaagctaca acagttcgag gagctactgg    420
acgtcgcatg gtgatgcgag agactgggat attctgcttg ccgttggtga ggtcacgaag    480
tccactgcgg gcggcaagat aactgcgagt atcaaatggg ggagccccgt gtcactgaag    540
gaatttttcc cggcggaaat ggaaggaatg cacacaaatc aatttcttgg cggtgcaggt    600
gttgccattg tggcgtccaa cgggaatctt gtgtaccctg tgcaggttac gaacaaaaag    660
aagcaagttt tttccaagat cttctactcg gaagacgagg gcaagacgtg gaagtttggg    720
gagggtagga gtgattttgg ctgctctgaa cctgtggccc ttgagtggga ggggaagctc    780
atcataaaca ctcgagttga ctatcgccgc cgtctggtgt acgagtccag tgacatgggg    840
aattcgtggg tggaggctgt cggcacgctc tcacgtgtgt ggggcccctc accaaaatcg    900
aaccagcccg gcagtcagag cagcttcact gccgtgacca tcgagggaat gcgtgttatg    960
ctcttcacac acccgctgaa ttttaaggga aggtggctgc gcgaccgact gaacctctgg   1020
ctgacggata accagcgcat ttataacgtt gggcaagtat ccattggtga tgaaaattcc   1080
gcctacagct ccgtcctgta caaggatgat aagctgtact gtttgcatga gatcaacagt   1140
aacgaggtgt acagccttgt ttttgcgcgc ctggttggcg agctacggat cattaaatca   1200
gtgctgcagt cctggaagaa ttgggacagc cacctgtcca gcatttgcac ccctgctgat   1260
ccagccgctt cgtcgtcaga gcgtggttgt ggtcccgctg tcaccacggt tggtcttgtt   1320
ggctttttgt cgcacagtgc caccaaaacc gaatgggagg atgcgtaccg ctgcgtcaac   1380
gcaagcacgg caaatgcgga gagggttccg aacggtttga agtttgcggg ggttggcgga   1440
```

-continued

```
ggggcgcttt ggccggtgag ccagcagggg cagaatcaac ggtatcactt tgcaaaccac   1500
gcgttcacgc tggtggcgtc ggtgacgatt cacgaggttc cgagcgtcgc gagtcctttg   1560
ctgggtgcga gcctggactc ttctggtggc aaaaaactcc tggggctctc gtacgacgag   1620
aagcaccagt ggcagccaat atacggatca acgccggtga cgccgaccgg atcgtgggag   1680
atgggtaaga ggtaccacgt ggttcttacg atggcgaata aaattggttc ggtgtacatt   1740
gatggagaac ctctggaggg ttcagggcag accgttgtgc cagacgggag gacgcctgac   1800
atctcccact tctacgttgg cgggtatgga aggagtgata tgccaaccat aagccacgtg   1860
acggtgaata atgttcttct ttacaaccgt cagctgaatg ccgaggagat caggaccttg   1920
ttcttgagcc aggacctgat tggcacggaa gcacacatgg gcagcagcag cggcagcagt   1980
gaaagaagta cgcccggatc cggctgctaa                                     2010
```

```

<210> SEQ ID NO 4
<211> LENGTH: 669
<212> TYPE: PRT
<213> ORGANISM: Artificial Sequence
<220> FEATURE:
<223> OTHER INFORMATION: Variant of T. Cruzi trans-sialidase protein.

<400> SEQUENCE: 4

Met Gly Ser Ser His His His His His His Ser Ser Gly Leu Val Pro
1               5                   10                  15

Arg Gly Ser His Met Ala Pro Gly Ser Ser Arg Val Glu Leu Phe Lys
            20                  25                  30

Arg Gln Ser Ser Lys Val Pro Phe Glu Lys Gly Gly Lys Val Thr Glu
        35                  40                  45

Arg Val Val His Ser Phe Arg Leu Pro Ala Leu Val Asn Val Asp Gly
    50                  55                  60

Val Met Val Ala Ile Ala Asp Ala Arg Tyr Glu Thr Ser Asn Asp Asn
65                  70                  75                  80

Ser Leu Ile Asp Thr Val Ala Lys Tyr Ser Val Asp Asp Gly Glu Thr
                85                  90                  95

Trp Glu Thr Gln Ile Ala Ile Lys Asn Ser Arg Ala Ser Ser Val Ser
            100                 105                 110

Arg Val Val Asp Pro Thr Val Ile Val Lys Gly Asn Lys Leu Tyr Val
        115                 120                 125

Leu Val Gly Ser Tyr Asn Ser Ser Arg Ser Tyr Trp Thr Ser His Gly
    130                 135                 140

Asp Ala Arg Asp Trp Asp Ile Leu Leu Ala Val Gly Glu Val Thr Lys
145                 150                 155                 160

Ser Thr Ala Gly Gly Lys Ile Thr Ala Ser Ile Lys Trp Gly Ser Pro
                165                 170                 175

Val Ser Leu Lys Glu Phe Phe Pro Ala Glu Met Glu Gly Met His Thr
            180                 185                 190

Asn Gln Phe Leu Gly Gly Ala Gly Val Ala Ile Val Ala Ser Asn Gly
        195                 200                 205

Asn Leu Val Tyr Pro Val Gln Val Thr Asn Lys Lys Lys Gln Val Phe
    210                 215                 220

Ser Lys Ile Phe Tyr Ser Glu Asp Glu Gly Lys Thr Trp Lys Phe Gly
225                 230                 235                 240

Glu Gly Arg Ser Asp Phe Gly Cys Ser Glu Pro Val Ala Leu Glu Trp
                245                 250                 255

Glu Gly Lys Leu Ile Ile Asn Thr Arg Val Asp Tyr Arg Arg Arg Leu
```

```
            260                 265                 270
Val Tyr Glu Ser Ser Asp Met Gly Asn Ser Trp Val Glu Ala Val Gly
            275                 280                 285

Thr Leu Ser Arg Val Trp Gly Pro Ser Pro Lys Ser Asn Gln Pro Gly
290                 295                 300

Ser Gln Ser Ser Phe Thr Ala Val Thr Ile Glu Gly Met Arg Val Met
305                 310                 315                 320

Leu Phe Thr His Pro Leu Asn Phe Lys Gly Arg Trp Leu Arg Asp Arg
                325                 330                 335

Leu Asn Leu Trp Leu Thr Asp Asn Gln Arg Ile Tyr Asn Val Gly Gln
                340                 345                 350

Val Ser Ile Gly Asp Glu Asn Ser Ala Tyr Ser Val Leu Tyr Lys
            355                 360                 365

Asp Asp Lys Leu Tyr Cys Leu His Glu Ile Asn Ser Asn Glu Val Tyr
            370                 375                 380

Ser Leu Val Phe Ala Arg Leu Val Gly Glu Leu Arg Ile Ile Lys Ser
385                 390                 395                 400

Val Leu Gln Ser Trp Lys Asn Trp Asp Ser His Leu Ser Ser Ile Cys
                405                 410                 415

Thr Pro Ala Asp Pro Ala Ala Ser Ser Glu Arg Gly Cys Gly Pro
                420                 425                 430

Ala Val Thr Thr Val Gly Leu Val Gly Phe Leu Ser His Ser Ala Thr
                435                 440                 445

Lys Thr Glu Trp Glu Asp Ala Tyr Arg Cys Val Asn Ala Ser Thr Ala
                450                 455                 460

Asn Ala Glu Arg Val Pro Asn Gly Leu Lys Phe Ala Gly Val Gly Gly
465                 470                 475                 480

Gly Ala Leu Trp Pro Val Ser Gln Gln Gly Gln Asn Gln Arg Tyr His
                485                 490                 495

Phe Ala Asn His Ala Phe Thr Leu Val Ala Ser Val Thr Ile His Glu
                500                 505                 510

Val Pro Ser Val Ala Ser Pro Leu Leu Gly Ala Ser Leu Asp Ser Ser
                515                 520                 525

Gly Gly Lys Lys Leu Leu Gly Leu Ser Tyr Asp Glu Lys His Gln Trp
530                 535                 540

Gln Pro Ile Tyr Gly Ser Thr Pro Val Thr Pro Thr Gly Ser Trp Glu
545                 550                 555                 560

Met Gly Lys Arg Tyr His Val Val Leu Thr Met Ala Asn Lys Ile Gly
                565                 570                 575

Ser Val Tyr Ile Asp Gly Glu Pro Leu Glu Gly Ser Gly Gln Thr Val
                580                 585                 590

Val Pro Asp Gly Arg Thr Pro Asp Ile Ser His Phe Tyr Val Gly Gly
                595                 600                 605

Tyr Gly Arg Ser Asp Met Pro Thr Ile Ser His Val Thr Val Asn Asn
                610                 615                 620

Val Leu Leu Tyr Asn Arg Gln Leu Asn Ala Glu Glu Ile Arg Thr Leu
625                 630                 635                 640

Phe Leu Ser Gln Asp Leu Ile Gly Thr Glu Ala His Met Gly Ser Ser
                645                 650                 655

Ser Gly Ser Ser Glu Arg Ser Thr Pro Gly Ser Gly Cys
                660                 665
```